(12) United States Patent
Elmaleh et al.

(10) Patent No.: US 7,438,893 B2
(45) Date of Patent: Oct. 21, 2008

(54) POLYBIOTIN COMPOUNDS FOR MAGNETIC RESONANCE IMAGING AND DRUG DELIVERY

(75) Inventors: David R. Elmaleh, Newton, MA (US); Timothy Shoup, Waltham, MA (US); Alan J. Fischman, Boston, MA (US)

(73) Assignee: Massachusetts General Hospital, Charlestown, MA (US)

( * ) Notice: Subject to any disclaimer, the term of this patent is extended or adjusted under 35 U.S.C. 154(b) by 384 days.

(21) Appl. No.: 10/956,687

(22) Filed: Oct. 1, 2004

(65) Prior Publication Data

US 2005/0136008 A1    Jun. 23, 2005

Related U.S. Application Data

(60) Provisional application No. 60/508,152, filed on Oct. 2, 2003.

(51) Int. Cl.
*A61B 5/055* (2006.01)
*C07F 5/00* (2006.01)
*C07D 235/02* (2006.01)

(52) U.S. Cl. .............. 424/9.36; 424/9.3; 424/9.363; 424/9.364; 424/9.365; 534/15; 548/304.1

(58) Field of Classification Search .......... 424/9.363, 424/9.3, 9.364, 9.635, 9.36; 534/15, 11; 540/474; 548/304.1
See application file for complete search history.

(56) References Cited

U.S. PATENT DOCUMENTS

| | | | |
|---|---|---|---|
| 5,980,862 A | 11/1999 | Meade et al. | |
| 6,120,768 A | 9/2000 | Griffiths et al. | |
| 7,141,676 B1 * | 11/2006 | Wilbur et al. | 548/303.7 |

* cited by examiner

*Primary Examiner*—Michael G. Hartley
*Assistant Examiner*—Leah Schlientz
(74) *Attorney, Agent, or Firm*—Beth E. Arnold; Foley Hoag LLP

(57) ABSTRACT

The invention relates generally to biotin-containing compounds that are useful as imaging agents and drug-delivery agents. Another aspect of the invention relates to the aforementioned compounds chelated to a metal atom. In a preferred embodiment, the metal atom is a gadolinium. Another aspect of the invention relates to a compound comprising three biotin moieties and a pharmaceutical agent covalently bound to a heterocyclic core. In certain embodiments, the pharmaceutical agent is an antibiotic, antiviral, or radionuclide. Another aspect of the present invention relates to a method of treating disease involving administering the compounds of the invention to a mammal. Another aspect of the present invention relates to a method of acquiring a magnetic resonance image using the compounds of the invention.

8 Claims, 2 Drawing Sheets

POLYBIOTIN COMPOUNDS FOR MAGNETIC RESONANCE IMAGING AND DRUG DELIVERY

RELATED APPLICATIONS

This application claims the benefit of priority to U.S. Provisional Patent Application Ser. No. 60/508,152, filed Oct. 2, 2003, the specifications of which is hereby incorporated in its entirety by this reference.

BACKGROUND OF THE INVENTION

Magnetic resonance imaging (MRI) is an imaging technique used primarily in clinical settings to produce very clear, detailed pictures of internal organs and tissues. These pictures are much more detailed than those from other scanning techniques. MRI began as a tomographic imaging method which produced an image of only a thin slice of the human body; however, MRI has advanced beyond this to become a volume imaging technique. The quality of images obtained using MRI can be increased by the i.v. administration of a contrast agent prior to the MRI exam. Contrast agents allow particular organs or tissues to be visualized more clearly by increasing the signal level of the particular organ or tissue relative to that of its surroundings.

One important application of magnetic resonance imaging is the visualization of tumors. One approach to obtaining high quality tumor images involves the use of antibodies that bind to the tumor cell. In one variant of this technique, a non-radiolabeled antibody is administered and allowed to localize and clear from the circulation followed a low molecular weight radiolabeled agent with high affinity for the pretargeted antibody (Paganelli, G. et al., J. Nucl. Med Comm. 12:211-234 (1991); Green, N M Biochem. J. 89:585-91 (1963); Hnatowich D J et al., J. Nucl. Med. 28:1294-1302 (1987)). Avidin, a cationic glycoprotein found in egg whites, has been used in tumor imaging in conjunction with biotin, a naturally occurring vitamin. Avidin has a very high affinity for biotin and is capable of binding four biotin molecules forming an avidin-biotin complex (Kd=10.sup.-15 M).

Two basic approaches for targeting tumors with the avidin-biotin system have been used in patients and animals. In the first method, avidin (or streptavidin)-conjugated antibodies are injected and days later when antibody-tumor binding is maximized, a radioactive biotin derivative is injected to localize the tumor. Unfortunately, incomplete clearance of unbound antibody from the blood can obscure visualization of the target site. In the second method, blood background is reduced by injecting biotinylated antibodies followed three days later by cold avidin. The resultant circulating biotinylated antibody-avidin complexes are sequestered from the blood by the liver. Radioactive biotin is then injected which binds to the antibody-biotin-avidin complexes already localized in the tumor. However, by employing "pretargetting" steps, both approaches for targeting tumors require that a subject be available to undergo multiple procedures over the course of a few days. A study by Morrel et al., reported uptake of In-111 labeled IgG and human serum albumin (HSA) in an *E. coli* infected rat model. The accumulation of both labeled proteins was found to be sufficient to produce clear images of the infection site (Morrel, E M et al., J. Nucl. Med. 30:1538-1545 (1989). In addition, the current biotin-avidin system suffers from slow target concentration and suboptimal target to non-target binding ratios which prevent acquisition of high-quality images owing to poor contrast and resolution.

Therefore, a need exists for robust imaging agents that bind with high specificity to tumor tissue to produce high-quality images.

In addition to obtaining high quality images in order to better treat cancer and other diseases, the successful recovery from an illness generally requires treating the patient with a therapeutic drug. One particularly problematic aspect of administering a pharmaceutical compound is the delivery of the compound to the desired tissue in the patient. This can be especially true in the treatment of canerous tissue by administration of a radionuclide. The radionuclide functions by releasing radiation which causes cells to die, hence, the radionuclide needs to be delivered quickly and specifically to the cancerous tissue to avoid harming healthy tissue. In response to this need, many strategies and materials have been developed to safely deliver a drug to diseased tissue. However, the need still exists to deliver pharmaceutical agents to diseased tissue with high selectivity.

SUMMARY OF THE INVENTION

The invention relates generally to biotin containing compounds that are useful as imaging agents and drug delivery agents. In certain embodiments, the compounds of the invention comprise a heterocyclic core to which three or four biotin moieties are attached. In a preferred embodiment, four biotin moieties are attached to a heterocyclic core comprising a 12-member ring. In certain embodiments, the biotin moiety is attached to the core by a tether comprising an amide bond. Another aspect of the invention relates to the aforementioned compound that is chelated to a metal atom. In a preferred embodiment, the metal atom is a gadolinium. Another aspect of the invention relates to a compound comprising three biotin moieties and a pharmaceutical agent covalently bound to a heterocyclic core. In certain embodiments, the pharmaceutical agent is an antibiotic, antiviral, or radionuclide. Another aspect of the present invention relates to a method of treating disease involving administering the compounds of the invention to a mammal. Another aspect of the present invention relates to a method of acquiring a magnetic resonance image using the compounds of the invention.

DETAILED DESCRIPTION OF THE INVENTION

Figure 1:
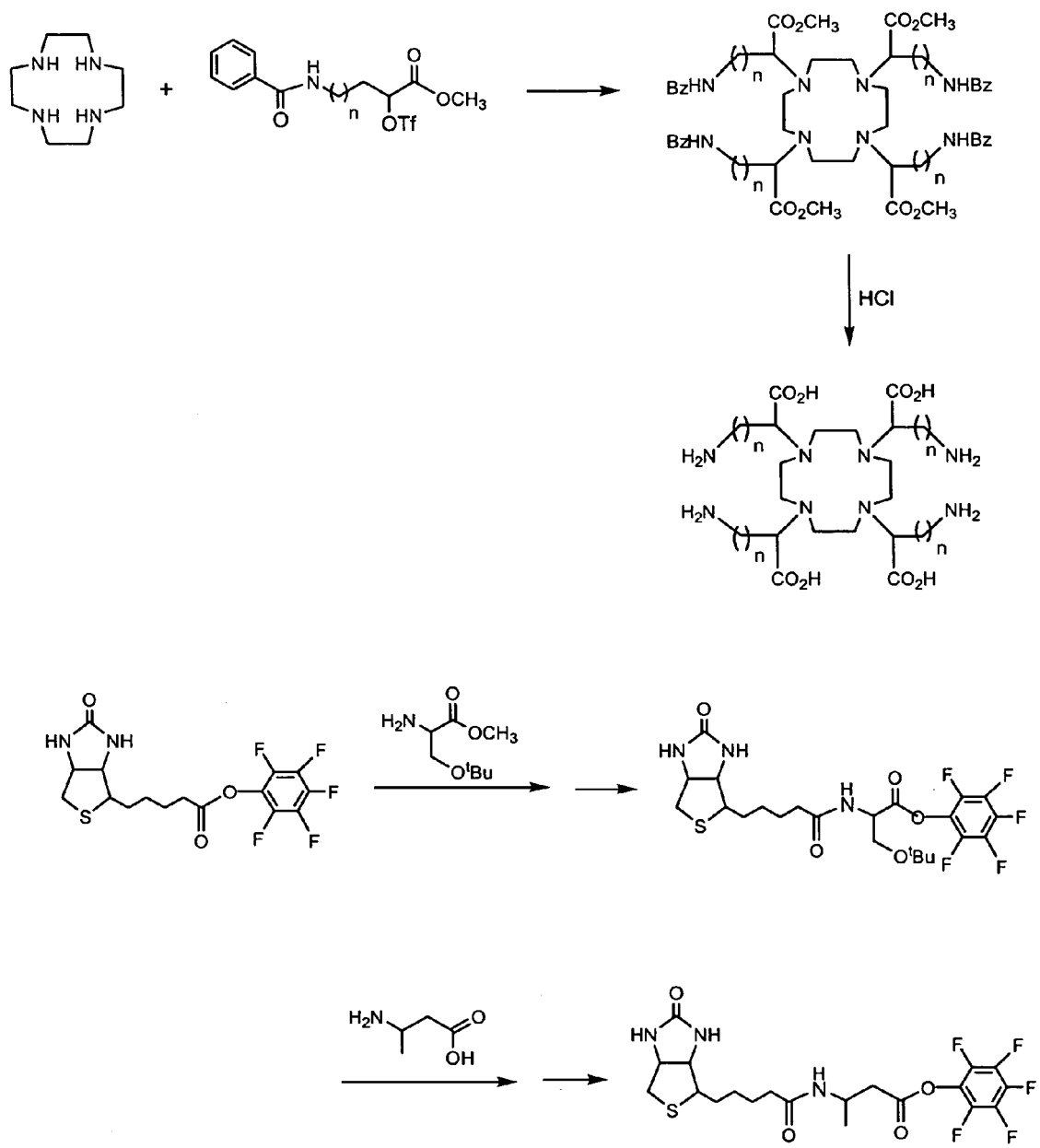
FIG. 1 depicts the synthesis of DOTA.
Figure 2:
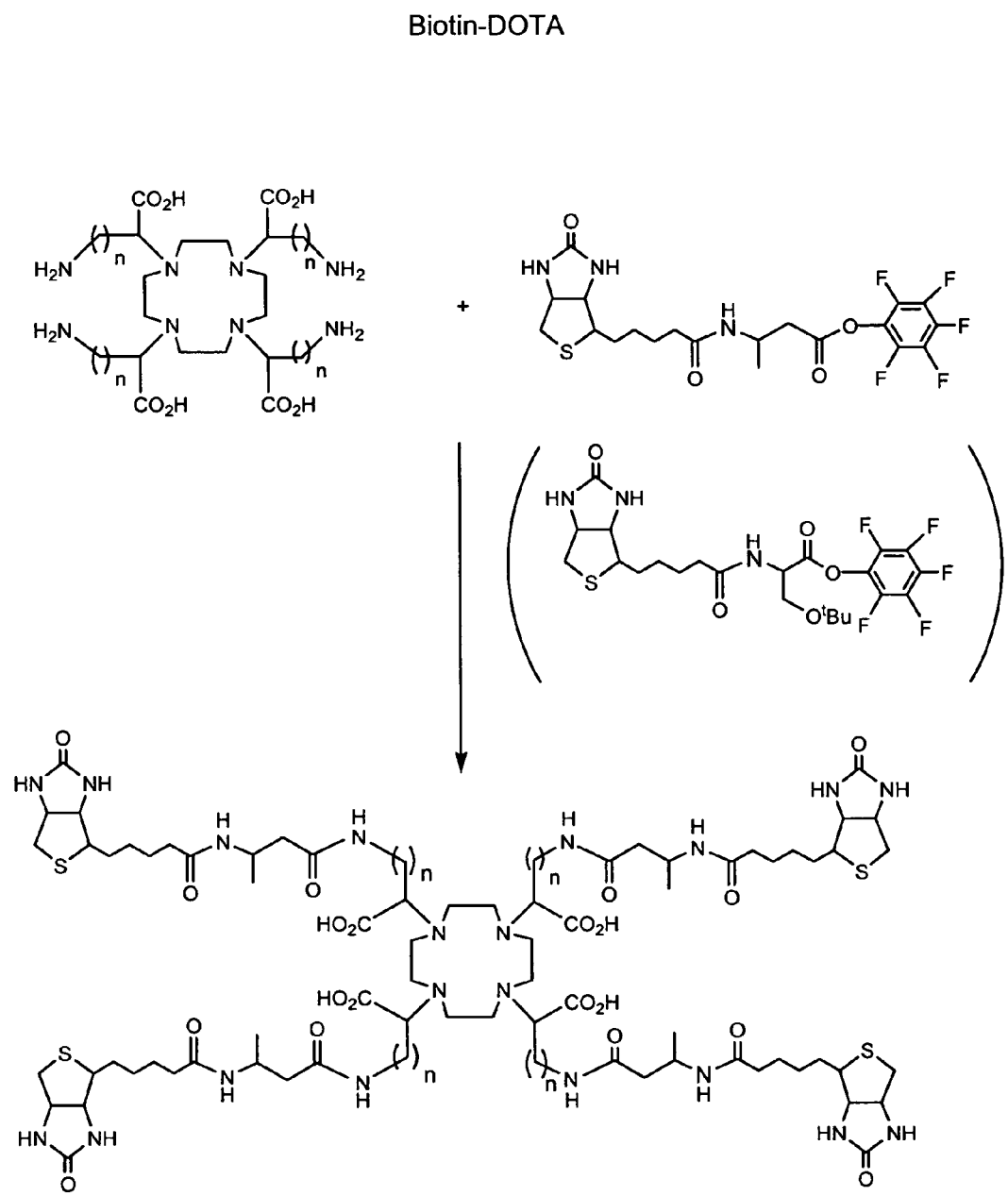
FIG. 2 depicts the synthesis of Biotin-DOTA.

The invention relates generally to biotin containing compounds that are useful as imaging agents and drug delivery agents. The compounds of the invention comprise a core scaffold to which at least one biotin group is attached. In preferred embodiments, three or four biotin groups are attached to the core scaffold. The biotin groups serve to direct the imaging agent or drug delivery agent to a desired site with higher specificity. In certain embodiments, the biotin groups are attached to the core scaffold by a tether comprising at least one amide bond. In a preferred embodiment, the tether is an alkyl group that contains two amide bond linkages. In certain embodiments, the core scaffold is a monocylic heteroalkyll group that forms an 8, 10, 12, 14, or 16 member ring. In a preferred embodiment, the core scaffold comprises a chelating group. In a more preferred embodiment, the core scaffold is a 12-member heteroalkyll ring containing four nitrogen atoms. In certain embodiments, the compound of the invention relates to the compound described above which is complexed to a metal atom. In certain embodiments, said metal atom is selected to give the complex superior properties as a MRI contrast agent. In certain embodiments, said metal atom is In-111, Tc-99m, I-123, I-125 F-18, Ga-67, or Ga-68. In certain embodiments, the metal atom is selected to give the complex superior properties as a cancer treatment drug. In a preferred embodiment, the metal atom is $^{90}$Y, $^{99m}$TC, $^{188}$Re, $^{32}$P, $^{166}$Ho, $^{109}$Pd, $^{140}$La, $^{153}$Sm, $^{165}$Dy, or $^{169}$Er. In a more preferred embodiment, the metal atom is $Gd^{3+}$, $Mn^{2+}$, $Fe^{3+}$, $Cr^{3+}$, dysprosium, holmium, or erbium.

In certain embodiments, an imaging group is covalently bound to the core scaffold. The term imaging group refers to a composition capable of generating a detectable image upon binding with a target. In certain embodiments, the imaging group contains a radionuclide such as In-111, Tc-99m, I-123, I-125 F-18, Ga-67, or Ga-68. The imaging group may be visualized using Positron Emission Tomography (PET) or Single Photon Emission Tomography (SPECT). In other embodiments, the imaging agent is an unpaired spin atom or free radical (e.g. Fe or Gd) or contrast agent (e.g. chelated (DTPA) manganese) for Magnetic Resonance Imaging (MRI). Additional contrast agents for Magnetic Resonance Imaging are described in the discussion below for MRI Contrast Agents.

In certain embodiments, a therapeutic group is covalently bound to the core scaffold. The term therapeutic group refers to an agent that is capable of treating a disease. In certain embodiments, the therapuetic group is capable of preventing the establishment or growth (systemic or local) of a tumor or infection. Examples include drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense nucleotides). Preferred therapeutic agents are drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense oligonucleotides that bind to a target nucleic acid sequence (e.g. mRNA sequence)), chemotherapeutic nucleotides, peptides, non-specific (non-antibody) proteins (e.g. sugar oligomers), boron containing compound (e.g. carborane), photodynamic agents (e.g. rhodamine 123), enediynes (e.g. calicheamicins, esperamicins, dynemicin, neocarzinostatin chromophore, and kedarcidin chromophore) and transcription based pharmaceuticals. In a preferred embodiment for treating or preventing the establishment or growth of a tumor, the therapeutic agent is a radionuclide, toxin, hormone antagonist, heavy metal complex, oligonucleotide, chemotherapeutic nucleotide, peptide, non-specific (non-antibody) protein, a boron compound or an enediyne. In a preferred embodiment for treating or preventing the establishment or growth of a bacterial infection, the therapeutic agent is an antibiotic, radionuclide or oligonucleotide. In a preferred embodiment for treating or preventing the establishment or growth of a viral infection, the therapeutic agent is an antiviral compound, radionuclide or oligonucleotide. In a preferred embodiment for treating or preventing the establishment or growth of a fungal infection, the therapeutic agent is an antifungal compound radionuclide or oligonucleotide.

Another aspect of the present invention relates generally to a method generating a magnetic resonance image of a human or animal body, comprising the steps of administering into the body of a subject in need of magnetic resonance imaging compound of the invention, and generating a magnetic resonance image. In certain embodiments, said compound comprises at least three biotin groups. In certain embodiments, said compound comprises gadolinium, technitium, or iodine. In a preferred embodiment, said compound comprises at least three biotin groups and gadolinium.

Another aspect of the present invention relates generally to a method treating a patient in need of a pharmaceutically effective amount of the compound of the invention in order to treat a disease. In certain embodiments, the disease is bacterial, viral, or fungal infenction. In certain embodiments, the disease is cancer. In certain embodiments, said compound comprises at least three biotin groups. In certain embodiments, said compound comprises a therapeutic group. In a preferred embodiment, the therapeutic group comprises a radionuclide, antibiotic, antiviral, or antifungal compound. In a preferred embodiment, the therapeutic group comprises a radionuclide. In a preferred embodiment, said compound comprises at least three biotin groups and gadolinium.

MRI Contrast Agents

Clinical imaging technology plays a significant role in diagnosis of injuries and disease processes. Many parts of the human body can now be examined using a variety of diagnostic imaging techniques. Radiography has long been used to image body parts through which externally generated x-rays are transmitted. Computerized axial tomography (CAT) provides cross-sectional x-ray images of a plane of the body. Specific tissues or organs may be targeted in positron emission tomography (PET), single photon emission computed tomography (SPECT), and gamma scintigraphy. In PET, SPECT, and gamma scintigraphy, radiopharmaceutical agents capable of being sequestered (concentrated) to some degree in the target tissue or organ are internally administered to the patient, and images are generated by detecting the radioactive emissions from the concentrated radiopharmaceutical agent. Some of the radiopharmaceutical agents currently used for imaging include nuclides such as $^{201}$Tl, $^{99m}$Tc, $^{133}$Xe, and the like; chelates of nuclides; radiolabeled metabolic agents such as $^{11}$C-deoxy-D-glucose, $^{18}$F-2-fluorodeoxy-D-glucose, [1-$^{11}$C]- and [$^{123}$I]-β-methyl fatty acid analogs, $^{13}$N-ammonia, and the like; infarct avid agents such as $^{99m}$Tc-tetracycline, $^{99m}$Tc-pyrophosphate, $^{203}$Hg-mercurials, $^{67}$Ga-citrate, and the like; and radiolabeled ligands, proteins, peptides, and monoclonal antibodies. Whole cells such as erythrocytes, platelets, leukocytes, and other cells may also be labeled with a radionuclide and function as radiopharmaceutical agents.

D. R. Elmaleh, et al. [(1984) Proc. Natl. Acad. Sci. USA 81, 918-921] disclosed the agent, $^{99m}$Tc-labeled Ap$_4$ A ($^{99m}$Tc-Ap$_4$ A), used to image tumors implanted in rats. Chelatation of $^{99m}$Tc to Ap$_4$ A in this study yielded a mixture, in which $^{99m}$Tc was attached to the Ap$_4$ A-dinucleotide and which also may have contained unchelated $^{99m}$Tc. This study was based on the premise that some human tumor cells are permeable to exogenous ATP and ADP, and that these cells incorporate the intact nucleotides in intracellular pools in contrast to normal cells. Ap$_4$ A was shown to permeate into hepatoma cells but not into a number of untransformed mammalian cell lines. In addition to accumulating in implanted tumors, $^{99m}$Tc-Ap$_4$ A in the 1984 study also accumulated in kidney, liver, bone, muscle, and lung.

The amount and type of clinical information that can be derived from PET, SPECT, and gamma scintigraphic images is related in part to the ability to concentrate the radiopharmaceutical agent in the target tissue or organ. Although many radiopharmaceuticals are available for clinical use, the resolution of the image generated may be limited depending on various factors. The resolution of a particular imaging agent for imaging diseased or injured tissue depends in part on the affinity of the radiopharmaceutical for the site of injury or disease as compared to its affinity for surrounding healthy tissue.

In MRI the contrast in the images generated may be enhanced by introducing into the zone being imaged an agent generally referred to as a contrast agent, which affects the spin reequilibration characteristics of the nuclei (the "imaging nuclei" which generally are protons and more specially water protons) which are responsible for the resonance signals from which the images are generated. The enhancement obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents. The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration coefficient known as $T_2$ or as the spin-spin relaxation time, a reduction arising from the effect on the imaging nuclei of the fields generated by the ferromagnetic or superparamagentic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself, and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ lowering effect is dominant. In either event, the relaxation time reduction results from the effect on the imaging nuclei of the magnetic fields generated by the paramagnetic centers.

The use of paramagnetic, ferromagnetic, and superparamagnetic materials as MRI contrast agents has been widely advocated and broad ranges of suitable materials have been suggested in the literature. For example Lauterbur and others have suggested the use of manganese salts and other paramagnetic inorganic salts and complexes (see Lauterbur et al. in "Frontiers of Biological Energetics", volume 1, pages 752-759, Academic Press (1978), Lauterbur in Phil. Trans. R. Soc. Lond. B289: 483-487 (1980) and Doyle et al. in J. Comput. Assist. Tomogr. 5(2): 295-296 (1981)). Runge et al. have suggested the use of particulate gadolinium oxalate (see for example U.S. Pat. No. 4,615,879 and Radiology 147(3): 789-791(1983)), Schering A G have suggested the use of paramagnetic metal chelates, for example of aminopolycarboxylic acids such as nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',—N'',N''-diethylenetriaminepentaacetic acid (DTPA), and 1,4,7,10-tetraazacyclododecanetetraacetic acid (DOTA) (see for example EP-A-71564, EP-A-130934, DE-A-3401052 and U.S. Pat. No. 4,639,365), and Nycomed AS have suggested the use of paramagnetic metal chelates of iminodiacetic acids (see EP-A-165728). Besides paramagnetic metals, paramagnetic stable free radicals have also been suggested for use as positive MRI contrast agents (see for example EP-A-133674).

Other paramagnetic MRI contrast agents are suggested or reviewed in, for example, EP-A-136812, EP-A-185899, EP-A-186947, EP-A-292689, EP-A-230893, EP-A-232751, EP-A-255471, WO85/05554, WO86/01112, WO87/01594, WO87/02893, U.S. Pat. Nos. 4,639,365, 4,687,659, 4,687,658, AJR 141: 1209-1215 (1983), Sem. Nucl. Med. 13: 364 (1983), Radiology 147: 781 (1983), J. Nucl. Med. 25: 506 (1984), WO89/00557 and International Patent Application No. PCT/EP89/00078.

Ferromagnetic (a term used herein to cover both ferrimagnetic and ferromagnetic materials) and superparamagnetic MRI contrast agents, for example sub-domain sized magnetic iron oxide particles either free or enclosed within or bound to a particle of a non-magnetic matrix material such as a polysaccharide, are disclosed by Schroder and Salford in WO85/02772, by Nycomed A S in WO85/04330, by Widder in U.S. Pat. No. 4,675,173, by Schering A G in DE-A-3443252 and by Advanced Magnetics Inc in WO88/00060.

Intravenous administration, at separate times, of the positive contrast agent Gd DTPA-dimeglumine (which following such administration rapidly distributes extracellularly) and of superparamagnetic ferrite particles was proposed by Weissleder et al. in AJR 150: 561-566 (1988) for imaging of liver cancers and by Carvlin et al. Society for Magnetic Resonance Imaging, 5th Annual Meeting, San Antonio, 1987, for studying renal blood flow. Carvlin and Weissleder's work on this topic is reported further in Proc. SPIE-Int. Soc. Opt. Eng. (1988) 914 Medical Imaging II, Pages 10-19 and AJR 150 115-120 (1988), respectively.

Fluorescence Imaging

Fluorescence is emitted when a fluorophore interacts with an incident photon (excitation). Absorption of the photon causes an electron in the fluorophore to rise from its ground state to a higher energy level. Then, the electron reverts to its original level, releasing a photon (fluorescence emission) whose wavelength depends upon the amount of energy that is released during reversion. A given fluorophore may emit at single or multiple wavelengths (creating an emission spectrum), as electrons drop from various orbitals to their ground states. The emission spectrum is constant for each species of fluorophore. Imaging finds many uses in fluorescence. As examples, consider the following: (1) An imaging system tuned to a specific emission spectrum can be used to localize a fluorophore. For example, cells expressing green fluorescent protein can be imaged and counted. (2) Changes in the fluorophore molecule (such as binding of fura-2 to Ca++) will lead to alterations in the emission spectrum. An imaging system can be used to measure these spectral changes, as an indication of changes in the environment of the fluorophore. (3) By measuring the intensity of fluorescence, an imaging system can estimate the concentration of a fluorescently tagged molecule. A common example of this is in the use of fluorescent microarrays for gene expression analyses.

Localization: Monochrome and Multispectral Fluorescence Imaging

In the simplest case (monochrome fluorescence imaging), a single fluorophore is used to mark a single molecular species. For example, glial fibrillary acidic protein (GFAP) labeled with fluorescein isothiocyanate (FITC) can be used to visualize regions of repair following CNS trauma. Similarly, a specific chromosomal DNA location can be shown by fluorescence in situ hybridization.

Multispectral fluorescence imaging demonstrates multiple molecular species in the same image. Each discrete fluorescent tag is visualized as a different color. For example, we might show Cy3 (green) and Cy5 (red), with the regions of overlap shown as mixtures of colors (e.g. red and green overlap shown as yellow). MCID® and AIS handle multispectral fluorescence in two ways.

For the best quality, each fluorophore is visualized independently, under optimal conditions. For example, discrete images of FITC and rhodamine fluorescence are created. The Image Fusion function then combines the two images into a single color image that shows inter-relationships among the tagged tissue components (Figure). This method yields the best image quality, for three reasons. First, high resolution, very sensitive cooled cameras can be used. Second, the fluorescence optics (e.g. excitation and emission filters) may be optimally tuned for each wavelength. Third, one has flexible control over the contribution of each discrete image to the final fused image.

For the most convenient operation, multiple fluorophores are visualized simultaneously. In this case, the optics provide simultaneous multispectral excitation and discrete emission wavelengths for each fluorophore. A color camera is used to image the multicolored specimen. As standard color cameras are not sufficiently sensitive to visualize fluorescence emission, an integrating color camera is used.

Quantification: Changes in Fluorophore Environment

Changes in pH, binding of the fluorophore to specific ions, and many other environmental factors can lead to an alteration in the emission spectrum of a fluorophore. Measurements of such changes were traditionally performed in cuvettes. However, various methods have been developed that allow imaging systems to be perform similar measurements at the cellular and subcellular levels. MCID includes dedicated functions for the quantification of changes in fluorophore environment.

Features in Fluorescence Imaging Systems

Typical fluorescence measurements include area and proportional area, number of fluorescent targets, and fluorescence intensity. The spatial measurements are quite straightforward, and are performed more or less well by most image analyzers. In contrast, intensity measurements can be rather tricky because fluorescence fades, and good calibration standards are difficult to create. MCID's proven competence in quantitative intensity measurement lets you concentrate on the specimens, not on the weaknesses of the measurement instrument. Importantly, standard video cameras are not well suited to fluorescence applications, and a specialized low-light camera is usually necessary. However, a broad variety of integrating cameras available for use with MCID and AIS.

Fluorescence Imaging Components

Intensified CCDs (ICCDs) consist of a video camera mated to an image intensifier. The intensifier amplifies incident illumination by an adjustable factor. ICCDs are fast, in that they take a short time image relatively dim specimens. Their main drawbacks are grainy images at high amplification, poor rendition of contrast in fine details, and a severely limited intra-scene dynamic range. That is, ICCDs cannot see both bright and dim material within one image (typical dynamic range of about 40:1). ICCDs are best suited to dynamic fluorescence imaging, where their ability to provide images quickly is a critical advantage. For most purposes, GEN IV intensifier is recommended, which exhibits much better image quality than other variants. Various ICCD cameras are available, but we recommend the Roper Instruments video ICCD with GEN IV intensifier, integrating CCD camera, and control unit. This is about as sensitive as a single-stage ICCD gets, and has the added benefit of being very flexible. For extremely dim specimens, multistage intensifiers are available, and are often used in photon counting applications. In our opinion, the trials of working with a multistage ICCD are significant, and it is preferable to use the Black Ice cryogenic integrating cameras when ultimate sensitivity is required.

Integrating cameras are like film. They accumulate incident illumination over time. In general, integrating cameras provide better image quality and broader dynamic range than intensified cameras. MCID and AIS support a variety of integrating cameras. Integrating video cameras are low in cost and suitable for moderately bright specimens such as many immunolabeled cells. For bright specimens, the camera does not need to be cooled. For dimmer specimens, chilled (above 0 degrees C.) or cooled (below 0 degrees C.) integrating video cameras are still cost-effective. However, do not expect any video camera to function with demanding specimens. Integrating video technology sacrifices sensitivity and dynamic range (limited to 8-10 bits) in exchange for low cost.

The next step above video is a family of moderately priced integrating cameras (e.g. the Roper Sensys or Hamamatsu 4742), which use high resolution CCDs that can be operated in integration mode. Typically, these cameras are chilled to above-zero temperatures, and make fine images with fluorescent specimens.

For more difficult specimens, scientific-grade, cooled cameras can be used. The exact definition of a "scientific grade" camera varies but, generally, these devices use full-coverage CCDs, high precision digitizers (>12 bits), and deep cooling. The most advanced of these cameras use special, high-sensitivity CCDs and cryogenic cooling (cool below −100 C). The Black Ice camera incorporates every technical advantage that known, to yield performance that is absolutely state-of-the-art. Unfortunately, Black Ice technology is costly, but there are many scientific-grade cameras that are reasonably priced and yield excellent performance.

The Imaging System

A single video frame (made in 1/30 sec) from an intensified camera will be very grainy. The quality of the low-light image is improved by real-time averaging. Therefore, ICCD cameras may be interfaced to any imaging system capable of rapid frame averaging. It is useful if the imaging system can also construct ratios and perform fluorescence background subtraction in real time.

Integrating cameras can present more of a challenge to the imaging system. Efficient use of an integrating camera presents the following requirements: (1) Integrated camera and software: Although MCID/AIS can use images from any camera (by importing TIFF files), it is convenient if the image analysis software also controls the various exposure and data transfer parameters of the camera. Doing image acquisition within dedicated camera software and image analysis in a separate package is very tedious. (2) Accept high precision data: The imaging system must accept and calibrate to data at high bit densities (integrating cameras supply data at 8-16 bits). (3) Fast interface: The imaging system should include a fast interface to the integrating camera. The best cameras come with a dedicated connection (e.g. RS422) to the imaging system interface board, or with their own interface card. Acquiring images via a SCSI or other slow connection is cheaper and easier for the manufacturer to implement, but really degrades imaging throughput.

MCID includes fast and efficient control of integrating cameras, and can be calibrated to high bit densities. AIS is more limited in the variety of cameras it supports, but retains the ability to use high bit densities and the direct control of supported integrating cameras.

Dynamic Fluorescence Imaging

MCID includes dedicated software for dynamic fluorescence as part of the standard image analysis package. This has two major benefits. a) The system that performs quantitative autoradiography, morphometry, and fluorescence densitometry can also perform ratiometric measurements without any additional software expense. b) Dynamic fluorescence imaging does not have to be learned as a discrete program. Rather, analysis, archiving, annotation, enhancement, and other operations are all easily performed on sequences of fluorescence images, using familiar MCID functions. MCID will acquire very large numbers of closely-spaced images directly into the computer. This on-line dynamic imaging is available with all of MCID's supported cameras, including ICCDs and integrating cameras.

Ratiometric Imaging

Ratiometric imaging takes advantage of the spectral shifts displayed when fluorescent dyes bind to their target ions. MCID supports various types of ratiometric imaging, including fura-2 imaging of calcium and BCECF imaging of pH.

The calcium chelator, fura-2, is used to measure cytosolic free Ca++ concentrations. The saturating calcium form of fura-2 has a maximum absorbance at about 335 NM. The calcium free form absorbs maximally at about 362 NM. The ratio (usually 340:380) of intensities of fluorescence changes by about an order of magnitude between saturated and calcium-free solutions. Thus, a relative brightening of the 340 image reflects an increase in the proportion of Fura-2 bound to Ca++.

Discrete 340 and 380 nm images are formed of cells incubated or injected with fura-2. The 340 and 380 nm images are corrected by the appropriate background, and a ratio image is formed. The ratio of 340 nm to 380 nm is passed through a simple equation (see below) to arrive at an estimate of Ca++ concentration.

Rmin is the ratio (340:380) of fluorescence intensity, formed at minimum Ca++ concentration. Rmax is the ratio (340:380) formed at saturating Ca++ concentration. F0/Fs is the ratio (380 nm) of fluorescence intensity at minimum and saturated Ca++ concentration. KD is the equilibrium dissociation constant for Ca++ and fura-2, usually stated as about 225 (Grynkiewicz, Poenie and Tsien, 1985; Williams and Fay, 1990). Each laboratory should calibrate the fura-2 technique under its own conditions. The ratio image can be displayed by using spectral color to represent calcium concentration. The ratio can also be displayed by modulating color and intensity independently. In this case, intensity reflects the intensity of the original component images (essentially equivalent to the confidence of the ratio at that point in the image), and color reflects calcium concentration.

A popular indicator dye for intracellular pH is BCECF (Rink, Tsien and Pozzan, 1982; Bright et al., 1987). BCECF fluoresces strongly at visible wavelengths, with an excitation peak at 503 nm and an emission peak at 525 nm. Both peaks are pH-dependent, being quenched by acidification and enhanced by more alkaline environments. At 436-439 nm, however, fluorescence is independent of pH. Therefore, a ratio can be constructed between pH-dependent and pH-independent BCECF images. In theory, this ratio will reflect pH independent of irrelevant influences such as dye concentration, illumination intensity, etc. A filter set for pH measurement with BCECF includes excitation filters at 440 and 495 nm, a 515 nm dichroic mirror and an emission filter at 535 nm. Backgrounds are acquired at 440 and 495 nm. All the procedures are as for Ca++ imaging. Ratios are passed through the following equation:

$$pH = pK + \log(R - R\text{max})(R\text{max} - R)$$

R is the normalized 495/440 nm fluorescence ratio, obtained as a ratio of the mean intensity value over any portion of the image, at each wavelength, at a pH of 7.0. One starts with a value of 7.17 for pK, and suggest that one calculate values appropriate for your conditions. BCECF is most commonly calibrated by using the K+/H+ ionophore, nigericin, to expose cells to known internal pHs (Thomas, et al., 1979).

To correct background fluorescence, one creates a ratio image from two excitation images (we will use 340 and 380 nm as examples). MCID offers three modes for correcting the excitation images prior to ratio formation: a) Subtractive: removal of background fluorescence and intensifier or camera offset. Background values for each of 340 and 380 nm images are entered. These background values are automatically subtracted from the 340 and 380 images before ratios are calculated. This is a simple, one-step correction, in that the same background error is applied over the entire field of view. b) Proportional: correction of shading error. Two independent, pixel-by-pixel shading corrections are applied; one for each excitation image. A blank field (the shading field) is acquired at each excitation. In both shading fields, each pixel's error is expressed as a proportion. Subsequent excitation images are corrected by the appropriate proportions before calculation of any ratios. c) Subtractive+proportional: Both subtractive and proportional shading correction can be used.

Flexible Excitation Conditions

A ratio image is calculated from images taken at two excitation wavelengths. In the simplest case, we take a single image at each excitation wavelength and then construct a ratio. However, any sequence of images may be acquired and processed before construction of a ratio. For example, one might construct a final image from a sequence of 340/380 alterations. This can avoid differential bleaching at one wavelength. One can also specify skipping of discrete excitation conditions. For example, a sequence of 20 timed ratios are taken, using 380 nm images taken every second. However, 340 nm images are taken only every three seconds.

Reading and Graphing Data from Multiple Ratio Images

Data from any number of timed ratios may be read simultaneously. By placing a sample tool onto a phase or DIC image, onto any excitation image, or onto any ratio image, MCID will report data across an entire experiment. The report will include any or all of:

gray level value at excitation 1 and 2
ratio
Ca++ concentration or other measurement Photometer Mode In some cases one does not need images. Rather one wishes to generate a single image, define regions of interest on that image and then have the system read ratios from those regions over time. It is as if one were using the imaging system as a photometer with multiple view windows. MCID allows any number of "photometer windows" to be placed on the image, and then reads the density values of these windows to construct the ratio.

Photometer mode generates a set of ratio and Ca++ concentration values across time. Any period of time may be used, and any number of regions may be read, as there are no memory storage requirements for the photometer data. The numerical values may be graphed, either during or following the acquisition process.

Adjusting the Two Excitation Wavelengths

Ideal ratiometric imaging requires that all images be acquired at near-equal intensities, well within the linear range of camera operation. Integrating cameras offer an elegant solution to the problem of balancing intensities. One can simply adjust the integration time differently for each excitation. This is quickly and easily done, using MCID's ratiometric functions.

There is more of a problem with ICCDs. ICCD brightness could be balanced by changing intensifier amplification (under computer control) for each wavelength. This is convenient but dangerous, unless intensifier response has been demonstrated to be linear across a range of amplification factors. Another option is to decrease fluorescence intensity at the brighter wavelength by using an ND filter mounted prior to the excitation filter. Various attenuation filters (e.g. 25%, 50%, 75%) may be mounted at different positions in the filter wheel, or in a second wheel. This option requires some fiddling with the filter wheel, but allows intensifier amplification to be maintained at a constant level.

Single Excitation, Single Emission

Single excitation, single emission procedures are much simpler than ratiometry. All that is necessary is that we acquire images at timed intervals, and then measure fluorescence intensity values from those images. Changes in fluor location escence intensity or fluor location (e.g. internalization of a receptor labeled with GFP) can be tracked. Changes in intensity are generally qualitative. That is, one can state that a change in fluorescence emission occurs, but one cannot quantify the change in terms of ionic concentrations.

An example of a single emission procedure is use of the Ca++ indicator fluo-3. It is excited at 503-506 nm, in the visible portion of the spectrum. Fluo-3 has a weaker affinity for Ca++ (KD about 400 nm) than do fura-2 or indo-1, permitting measurement of lower Ca++ concentrations. It also exhibits very marked changes in fluorescence intensity (about 4 decades) with Ca++ binding. Compare this with the tenfold change in fluorescence intensity exhibited by fura-2. MCID's single emission option is similar in use to fura-2 imaging, though there is only one excitation wavelength. As filter wheel changes are not required, rather short inter-image intervals are possible.

Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

When a straight chain or branched chain alkyl is refered to as optionally substituted it is understood to mean that at one or more positions the alkyl group is substituted with such substituents as described below, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, floronated alkysl, and nitriles.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

As used herein, the term "nitro" means —NO₂; the term "halogen" designates —F, —Cl, —Br or —I; the term "sulfhydryl" means —SH; the term "hydroxyl" means —OH; and the term "sulfonyl" means —SO₂—.

The terms "amine" and "amino" are art-recognized and refer to both unsubstituted and substituted amines, e.g., a moiety that can be represented by the general formula:

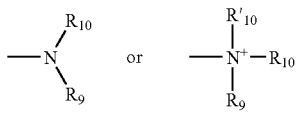

wherein $R_9$, $R_{10}$ and $R'_{10}$ each independently represent a group permitted by the rules of valence.

The term "acylamino" is art-recognized and refers to a moiety that can be represented by the general formula:

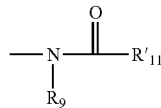

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

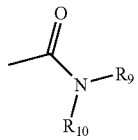

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

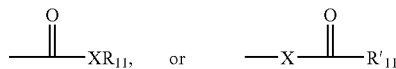

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}$' is hydrogen, the formula represents a "thiolformate." On the other hand, Where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

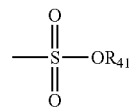

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

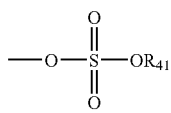

in which $R_{41}$ is as defined above.

The term "sulfonylamino" is art recognized and includes a moiety that can be represented by the general formula:

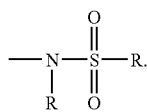

The term "sulfamoyl" is art-recognized and includes a moiety that can be represented by the general formula:

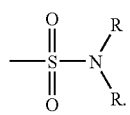

The term "sulfonyl", as used herein, refers to a moiety that can be represented by the general formula:

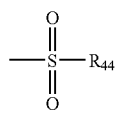

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

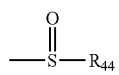

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: N.Y., 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Compounds of the Invention

One aspect of the present invention relates to a compound represented by formula I:

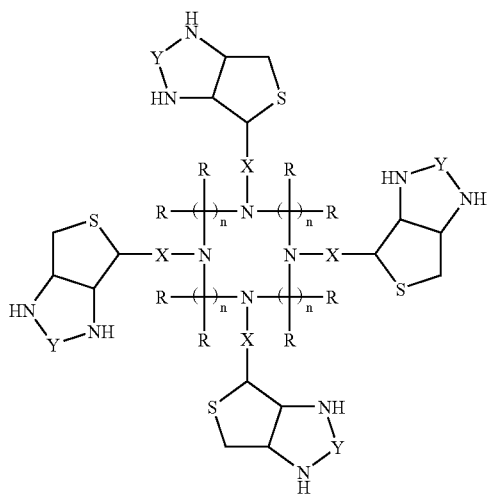

I wherein
R represents independently for each occurrence H or alkyl;
Y represents independently for each occurrence —C(O)— or —S(O)—;
n represents independently for each occurrence 1, 2, 3, or 4; and
X represents independently for each occurrence alkyl, heteroalkyl, alkenyl, or -[(alkyl-NR$^1$C(O))$_m$-alkyl]-, wherein m is 1, 2, 3, or 4; and R$^1$ is H or alkyl.

In certain embodiments, the present invention relates to compound I, wherein Y represents independently for each occurrence —C(O)—.

In certain embodiments, the present invention relates to compound I, wherein n represents independently for each occurrence 2.

In certain embodiments, the present invention relates to compound I, wherein n represents independently for each occurrence 2 and R represents independently for each occurrence hydrogen.

In certain embodiments, the present invention relates to compound I, wherein n represents independently for each occurrence 2, R represents independently for each occurrence hydrogen, and Y is —C(O)—.

In certain embodiments, the present invention relates to compound I, wherein X represents independently for each occurrence -[(alkyl-NR$^1$C(O))$_m$-alkyl]-.

In certain embodiments, the present invention relates to compound I, wherein X represents independently for each occurrence -[((C$_1$-C$_5$)alkyl-NR$^1$C(O))$_m$—(C$_1$-C$_5$)alkyl]-.

In certain embodiments, the present invention relates to compound I, wherein X represents independently for each occurrence -[(alkyl-NR$^1$C(O))$_m$-alkyl]-, m is 2, and R$^1$ is H.

In certain embodiments, the present invention relates to compound I, wherein X represents independently for each occurrence:

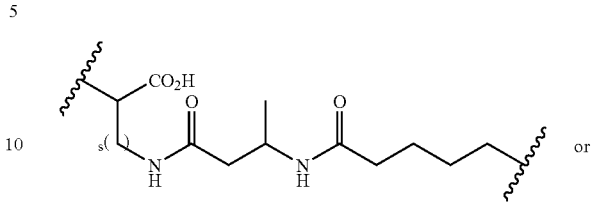

or

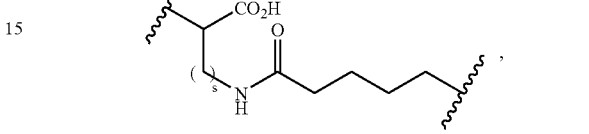

wherein s is 1, 2, 3 or 4.

In certain embodiments, the present invention relates to compound I, wherein X represents independently for each occurrence:

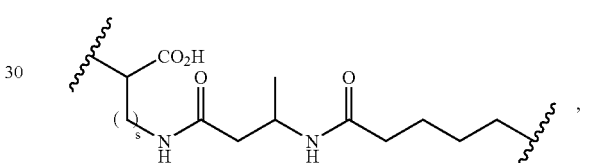

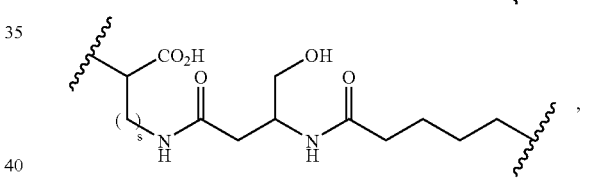

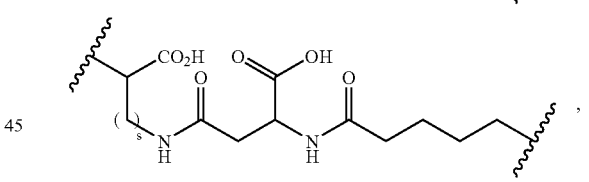

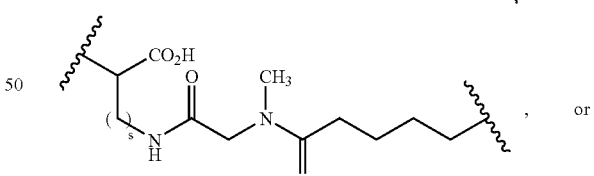

or

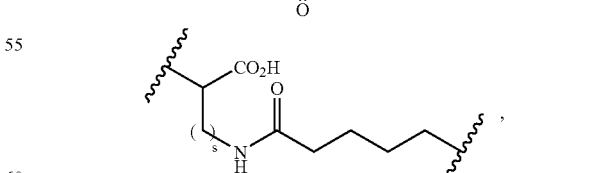

wherein s is 3 or 4.

In certain embodiments, the present invention relates to compound I, wherein X represents independently for each occurrence:

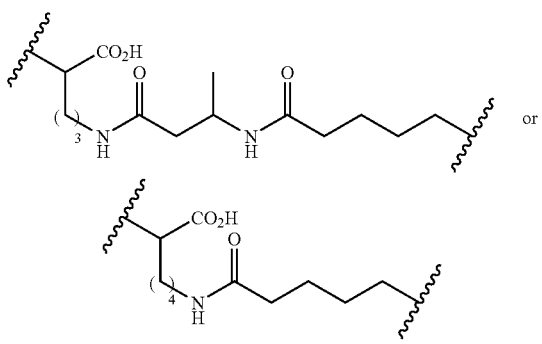

In certain embodiments, the present invention relates to compound I, wherein n represents independently for each occurrence 2, R represents independently for each occurrence hydrogen, Y is —C(O)—, and X represents independently for each occurrence:

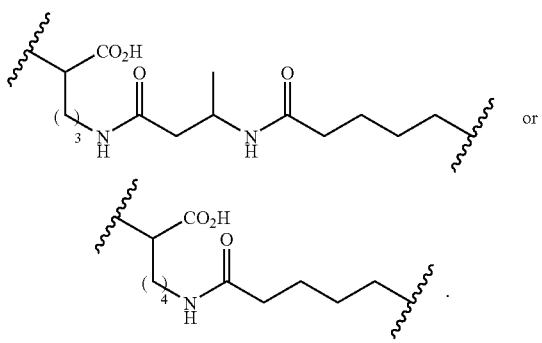

Another aspect of the present invention relates to a compound represented by formula II:

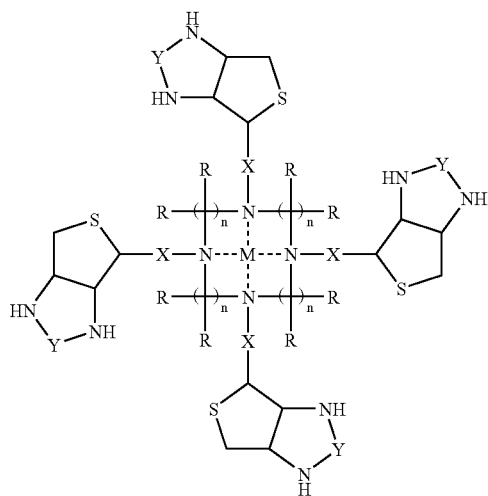

wherein
R represents independently for each occurrence H or alkyl;
Y represents independently for each occurrence —C(O)— or —S(O)—;
n represents independently for each occurrence 1, 2, 3, or 4;
M is a metal atom; and
X represents independently for each occurrence alkyl, heteroalkyl, alkenyl, or -[(alkyl-$NR^1C(O))_m$-alkyl]-, wherein m is 1, 2, 3, or 4; and $R^1$ is H or alkyl.

In certain embodiments, the present invention relates to compound II, wherein M is a transition metal.

In certain embodiments, the present invention relates to compound II, wherein M selected from the group consisting of In-111, Tc-99m, I-123, I-125 F-18, Ga-67, Ga-68, I-131, Re-186, Re-188, Y-90, Bi-212, At-211, Sr-89, Ho-166, Sm-153, Cu-67 and Cu-64.

In certain embodiments, the present invention relates to compound II, wherein M selected from the group consisting of Tc-99m, Ga-67, and Ga-68.

In certain embodiments, the present invention relates to compound II, wherein M selected from the group consisting of $Gd^{3+}$, $Mn^{2+}$, $Fe^{3+}$, $Cr^{3+}$, dysprosium, holmium, and erbium.

In certain embodiments, the present invention relates to compound II, wherein M selected from the group consisting of $Gd^{3+}$, $Mn^{2+}$, $Fe^{3+}$, and $Cr^{3+}$.

In certain embodiments, the present invention relates to compound II, wherein Y represents independently for each occurrence —C(O)—.

In certain embodiments, the present invention relates to compound II, wherein n represents independently for each occurrence 2.

In certain embodiments, the present invention relates to compound II, wherein n represents independently for each occurrence 2 and R represents independently for each occurrence hydrogen.

In certain embodiments, the present invention relates to compound II, wherein n represents independently for each occurrence 2, R represents independently for each occurrence hydrogen, and Y is —C(O)—.

In certain embodiments, the present invention relates to compound II, wherein X represents independently for each occurrence -[(alkyl-$NR^1C(O))_m$-alkyl]-.

In certain embodiments, the present invention relates to compound II, wherein X represents independently for each occurrence -[(($C_1$-$C_5$)alkyl-$NR^1C(O))_m$—($C_1$-$C_5$)alkyl]-.

In certain embodiments, the present invention relates to compound II, wherein X represents independently for each occurrence -[(alkyl-$NR^1C(O))_m$-alkyl]-, m is 2, and $R^1$ is H.

In certain embodiments, the present invention relates to compound I, wherein X represents independently for each occurrence:

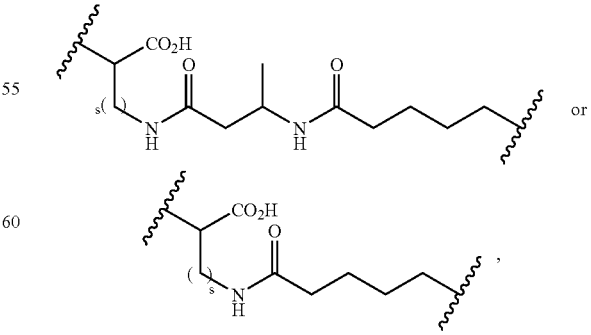

wherein s is 1, 2, 3 or 4.

In certain embodiments, the present invention relates to compound I, wherein X represents independently for each occurrence:

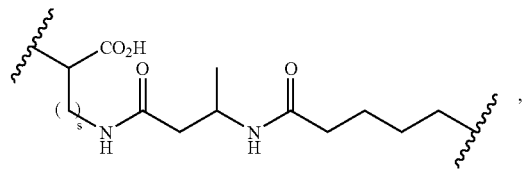,

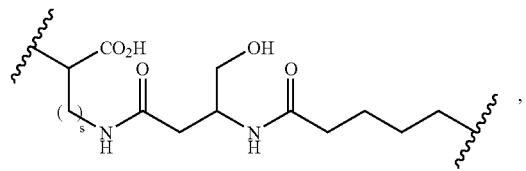,

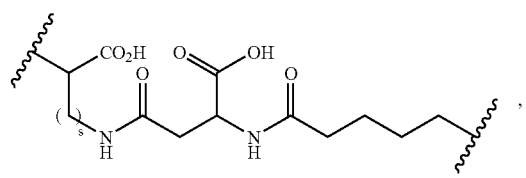,

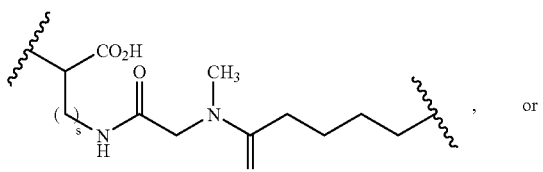 or

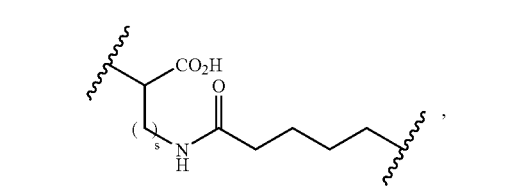, wherein s is 3 or 4.

In certain embodiments, the present invention relates to compound I, wherein X represents independently for each occurrence:

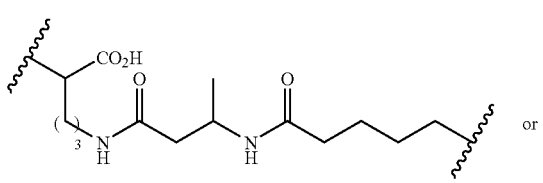 or

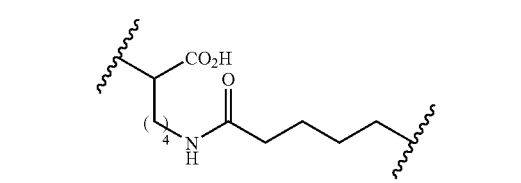

In certain embodiments, the present invention relates to compound I, wherein n represents independently for each occurrence 2, R represents independently for each occurrence hydrogen, Y is —C(O)—, and X represents independently for each occurrence:

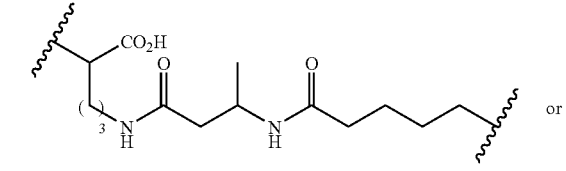 or

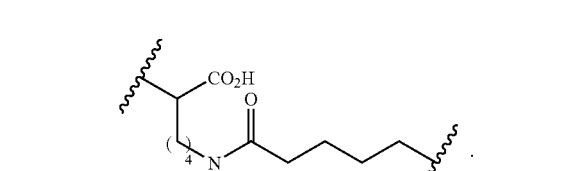.

In certain embodiments, the present invention relates to compound II, wherein X represents independently for each occurrence:

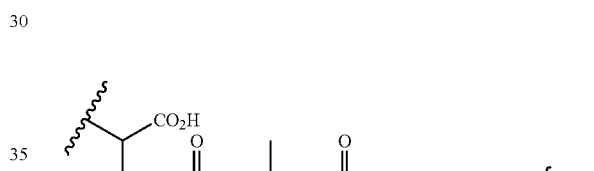 or

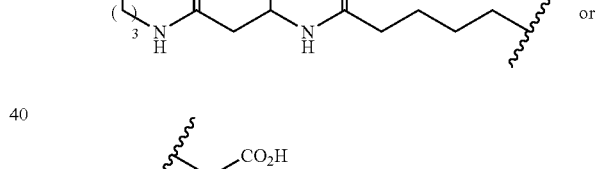, and the $CO_2H$ is coordinated to M.

In certain embodiments, the present invention relates to compound II, wherein n represents independently for each occurrence 2, R represents independently for each occurrence hydrogen, Y is —C(O)—, M is $Gd^{3+}$, and X represents independently for each occurrence:

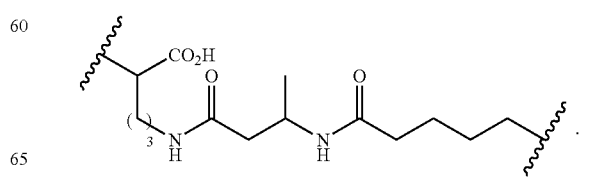

Another aspect of the present invention relates to a compound represented by formula III:

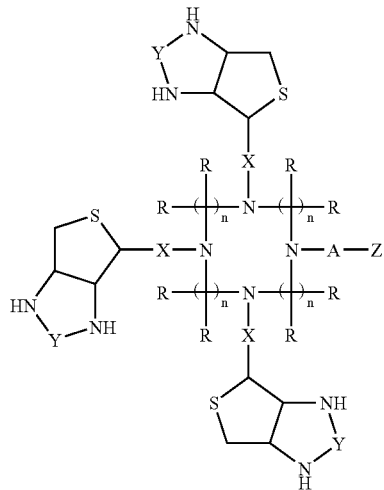

III wherein
R represents independently for each occurrence H or alkyl;
Y represents independently for each occurrence —C(O)— or —S(O)—;
n represents independently for each occurrence 1, 2, 3, or 4;
A is selected from the group consisting of a covalent bond, alkyl, heteroalkyl, alkenyl, or -[(alkyl-NR$^1$C(O))$_m$-alkyl]-, wherein m is 1, 2, 3, or 4; and R$^1$ is H or alkyl;
X represents independently for each occurrence alkyl, heteroalkyl, alkenyl, or -[(alkyl-NR$^1$C(O))$_m$-alkyl]-, wherein m is 1, 2, 3, or 4; and R$^1$ is H or alkyl; and
Z is —(CH)$_2$CO$_2$H, an antibiotic, anti-viral, anti-tumor, anti-inflammatory, anti-infective, antifungal, radionuclide, hormone antagonist, heavy metal complexes, oligonucleotide, antisense, chemotherapeutic nucleotide, peptide, protein, polysaccharide, aminoglycoside, antibody and fragments, lipid construct, non-specific (non-antibody) protein, boron containing compound, photodynamic agent, enediyne, or transcription based pharmaceutical.

In certain embodiments, the present invention relates to compound III, wherein Y represents independently for each occurrence —C(O)—.

In certain embodiments, the present invention relates to compound III, wherein n represents independently for each occurrence 2.

In certain embodiments, the present invention relates to compound III, wherein n represents independently for each occurrence 2 and R represents independently for each occurrence hydrogen.

In certain embodiments, the present invention relates to compound III, wherein n represents independently for each occurrence 2, R represents independently for each occurrence hydrogen, and A is a covalent bond.

In certain embodiments, the present invention relates to compound III, wherein n represents independently for each occurrence 2, R represents independently for each occurrence hydrogen, and Y is —C(O)—.

In certain embodiments, the present invention relates to compound III, wherein X represents independently for each occurrence -[(alkyl-NR$^1$C(O))$_m$-alkyl]-.

In certain embodiments, the present invention relates to compound III, wherein X represents independently for each occurrence -[((C$_1$-C$_5$)alkyl-NR$^1$C(O))$_m$—(C$_1$-C$_5$)alkyl]-.

In certain embodiments, the present invention relates to compound III, wherein X represents independently for each occurrence -[(alkyl-NR$^1$C(O))$_m$-alkyl]-, m is 2, and R$^1$ is H.

In certain embodiments, the present invention relates to compound III, wherein X represents independently for each occurrence -[((C$_1$-C$_5$)alkyl-NR$^1$C(O))$_m$—(C$_1$-C$_5$)alkyl]-, m is 2, and R$^1$ is H.

In certain embodiments, the present invention relates to compound III, wherein X represents independently for each occurrence:

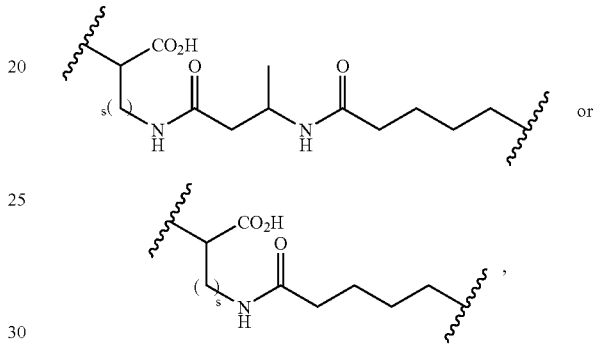

wherein s is 1, 2, 3 or 4.

In certain embodiments, the present invention relates to compound III, wherein X represents independently for each occurrence:

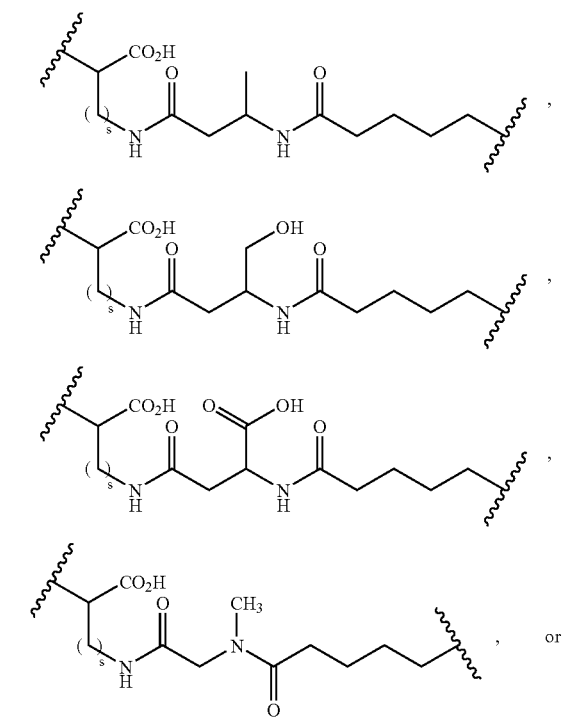

-continued

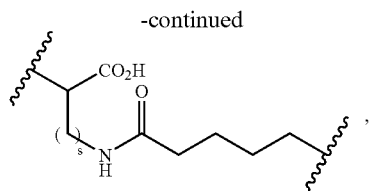

wherein s is 3 or 4.

In certain embodiments, the present invention relates to compound III, wherein X represents independently for each occurrence:

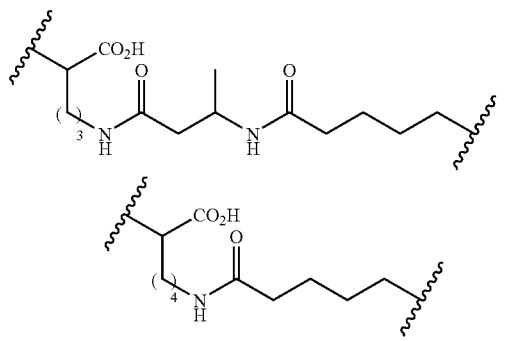

or

In certain embodiments, the present invention relates to compound III, wherein n represents independently for each occurrence 2, R represents independently for each occurrence hydrogen, Y is —C(O)—, and X represents independently for each occurrence:

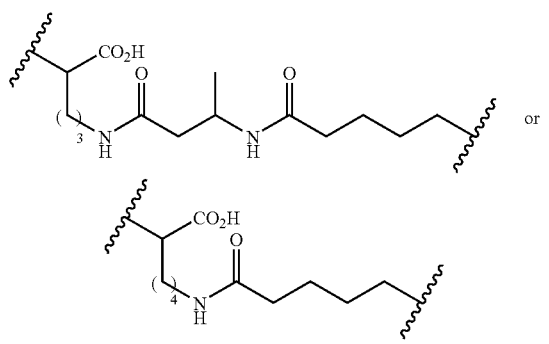

or

In certain embodiments, the present invention relates to compound III, wherein n represents independently for each occurrence 2, R represents independently for each occurrence hydrogen, Y is —C(O)—, A is a covalent bond, and X represents independently for each occurrence:

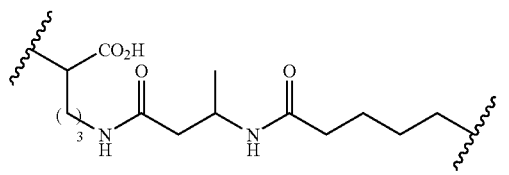

or

-continued

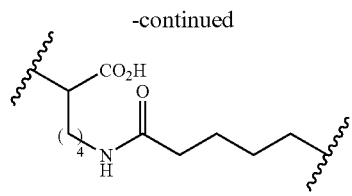

In certain embodiments, the present invention relates to compound III, wherein n represents independently for each occurrence 2, R represents independently for each occurrence hydrogen, Y is —C(O)—, Z is an anti-infectived, and X represents independently for each occurrence:

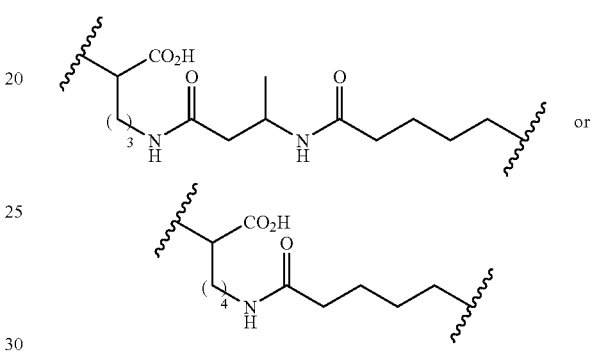

or

In certain embodiments, the present invention relates to compound III, wherein n represents independently for each occurrence 2, R represents independently for each occurrence hydrogen, Y is —C(O)—, Z is an anti-tumor, and X represents independently for each occurrence:

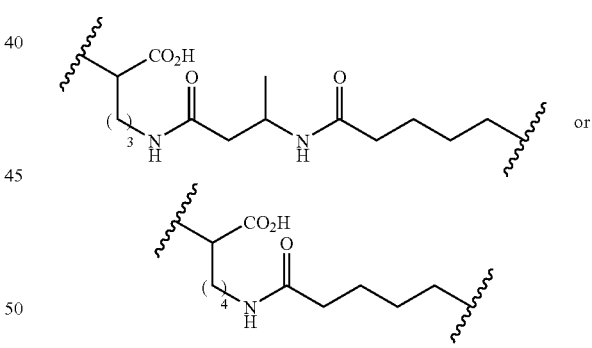

or

In certain embodiments, the present invention relates to compound III, wherein n represents independently for each occurrence 2, R represents independently for each occurrence hydrogen, Y is —C(O)—, Z is an anti-inflammatory, and X represents independently for each occurrence:

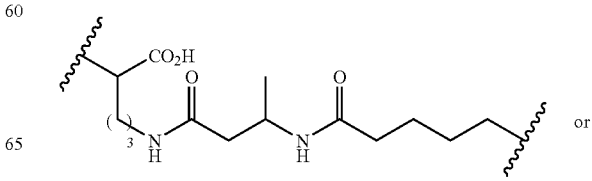

or

-continued

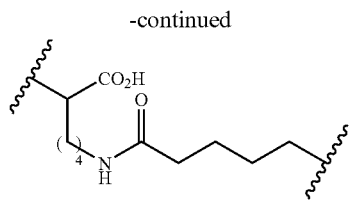

In certain embodiments, the present invention relates to compound III, wherein Z is an anti-infective, anti-inflammatory, or anti-tumor agent.

In certain embodiments, the present invention relates to compound III, wherein Z is selected from the group consisting of abacavir sulfate, abarelix, acarbose, acetaminophen, acetylsalicylic acid, acitretin, activated protein C, acyclovir, adefovir dipivoxil, adenosine, adrenocorticotrophic hormone, albuterol, alendronate sodium, allopurinal, alpha 1 proteinase inhibitor, alprazalom, alprostadil, altinicline, amifostine, amiodarone, amitriptyline HCL, amlodipine besylate, amoxicillin, amprenavir, anagrelide hydrochloride, anaritide, anastrozole, antisense oligonucleotide, aripiprazole, astemizole, atenolol, bupropion hydrochloride, buspirone, butorphanol tartrate, cabergoline, caffiene, calcitriol, candesartan, cilexetil, candoxatril, capecitabine, captopril, carbamazepine, carbidopa/Levodopa, carboplatin, carisoprodol, carvedilol, caspofungin, cefaclor, cefadroxil, cyclosporine, dalteparin sodium, dapitant, desmopressin acetate, diazepam, ABT 594, diclofenac sodium, dicyclomine HCL, didanosine, digoxin, diltiazem hydrochloride, fentanyl, fexofenadine hydrochloride, filgrastim SD01, finasteride, flecainide acetate, fluconazole, fludrocortisone acetate, flumazenil, fluoxetine, flutamide, fluvastatin, fluvoxamine maleate, follitropin alfa/beta, formoterol, fosinopril, fosphenytoin sodium, furosemide, gabapentin, gadodiamide, gadopentetate dimeglumine, gadoteridol, ganaxolone, ganciclovir, gantofiban, gastrin CW17 immunogen, gemcitabine hydrochloride, gemfibrozil, gentamicin isoton, gepirone hydrochloride, pioglitazone hydrochloride, piperacillin sodium, pleconaril, poloxamer CW188, posaconazole, NN 304, pramipexole dihydrochloride, pravastatin sodium, prednisone, pregabalin, primidone, prinomastat, prochlorperazine maleate, valdecoxib, valproic acid, valsartan hydrochlorothiazide, valspodar, Vancomycin HCL, Vecuronium bromide, venlafaxine hydrochloride, verapamil HCL, vinorelbine tartrate, vitamin B12, vitamin C, voriconazole, warfarin sodium, xaliproden, and zafirlukast.

In certain embodiments, the present invention relates to compound III, wherein A is:

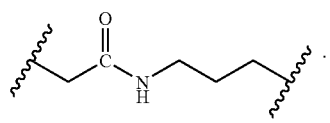

In certain embodiments, the present invention relates to compound III, wherein Z is selected from the group consisitng of an anti-infective, anti-inflammatory, and anti-tumor agent; and A is:

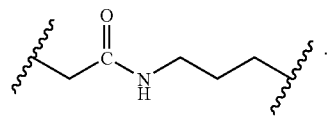

Another aspect of the present invention relates to a compound represented by formula IV:

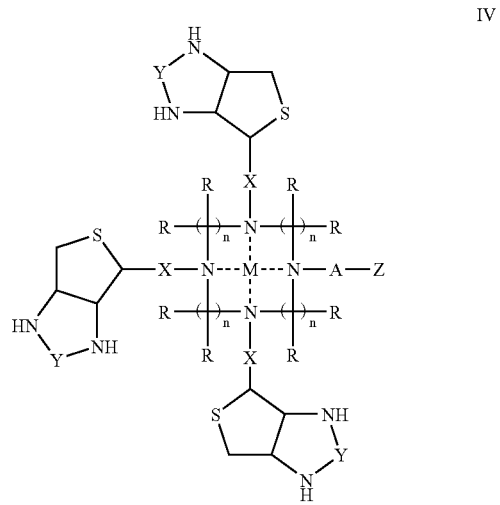

wherein
R represents independently for each occurrence H or alkyl;
Y represents independently for each occurrence —C(O)— or —S(O)—;
n represents independently for each occurrence 1, 2, 3, or 4;
M is a metal atom;
A is selected from the group consisting of a covalent bond, alkyl, heteroalkyl, alkenyl, or -[(alkyl-NR$^1$C(O))$_m$-alkyl]-, wherein m is 1, 2, 3, or 4; and R$^1$ is H or alkyl;
X represents independently for each occurrence alkyl, heteroalkyl, alkenyl, or -[(alkyl-NR$^1$C(O))$_m$-alkyl]-, wherein m is 1, 2, 3, or 4; and R$^1$ is H or alkyl;
a functional group of X is or is not coordinated to M; and
Z is —CH$_2$CO$_2$H, an antibiotic, anti-viral, anti-tumor, anti-inflammatory, anti-infective, antifungal, radionuclide, hormone antagonist, heavy metal complexes, oligonucleotide, antisense, chemotherapeutic nucleotide, peptide, protein, polysaccharide, aminoglycoside, antibody and fragments, lipid construct, non-specific (non-antibody) protein, boron containing compound, photodynamic agent, enediyne, or transcription based pharmaceutical.

In certain embodiments, the present invention relates to compound IV, wherein Y represents independently for each occurrence —C(O)—.

In certain embodiments, the present invention relates to compound IV, wherein n represents independently for each occurrence 2.

In certain embodiments, the present invention relates to compound IV, wherein n represents independently for each occurrence 2 and R represents independently for each occurrence hydrogen.

In certain embodiments, the present invention relates to compound IV, wherein n represents independently for each occurrence 2, R represents independently for each occurrence hydrogen, and A is a covalent bond.

In certain embodiments, the present invention relates to compound IV, wherein n represents independently for each occurrence 2, R represents independently for each occurrence hydrogen, and Y is —C(O)—.

In certain embodiments, the present invention relates to compound IV, wherein X represents independently for each occurrence -[(alkyl-NR$^1$C(O))$_m$-alkyl]-.

In certain embodiments, the present invention relates to compound IV, wherein X represents independently for each occurrence -[((C$_1$-C$_5$)alkyl-NR$^1$C(O))$_m$—(C$_1$-C$_5$)alkyl]-.

In certain embodiments, the present invention relates to compound IV, wherein X represents independently for each occurrence -[(alkyl-NR$^1$C(O))$_m$-alkyl]-, m is 2, and R$^1$ is H.

In certain embodiments, the present invention relates to compound IV, wherein X represents independently for each occurrence -[((C$_1$-C$_5$)alkyl-NR$^1$C(O))$_m$—(C$_1$-C$_5$)alkyl]-, m is 2, and R$^1$ is H.

In certain embodiments, the present invention relates to compound IV, wherein X represents independently for each occurrence -[((C$_1$-C$_5$)alkyl-NR$^1$C(O))$_m$—(C$_1$-C$_5$)alkyl]-, m is 2, R$^1$ is H, and A is a covalent bond.

In certain embodiments, the present invention relates to compound IV, wherein X represents independently for each occurrence:

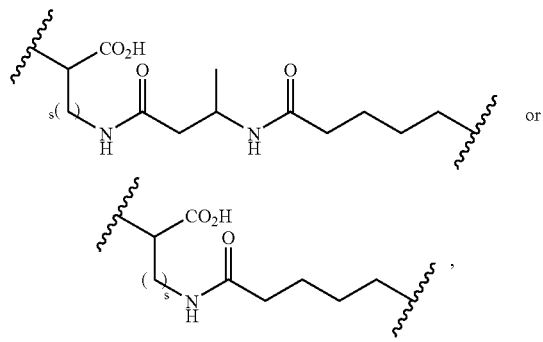

wherein s is 1, 2, 3 or 4.

In certain embodiments, the present invention relates to compound IV, wherein X represents independently for each occurrence:

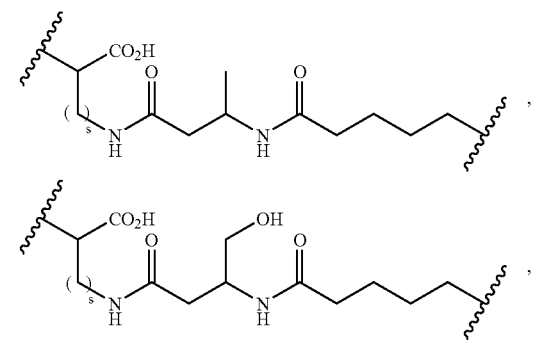

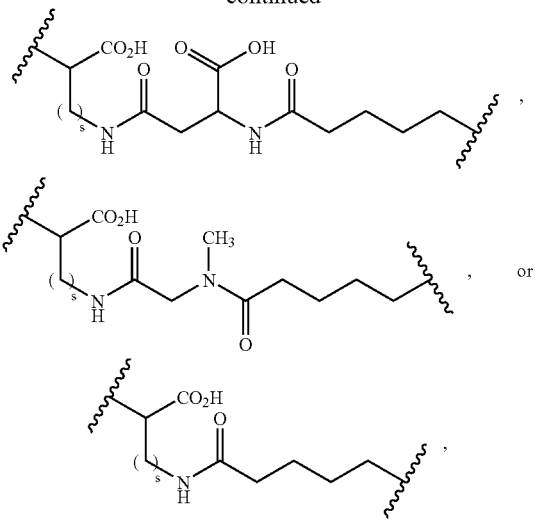

wherein s is 3 or 4.

In certain embodiments, the present invention relates to compound IV, wherein X represents independently for each occurrence:

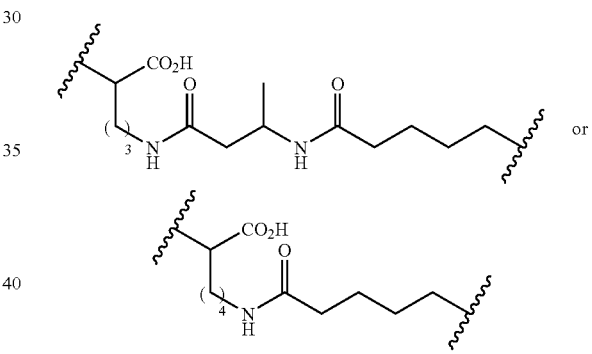

In certain embodiments, the present invention relates to compound IV, wherein n represents independently for each occurrence 2, R represents independently for each occurrence hydrogen, Y is —C(O)—, and X represents independently for each occurrence:

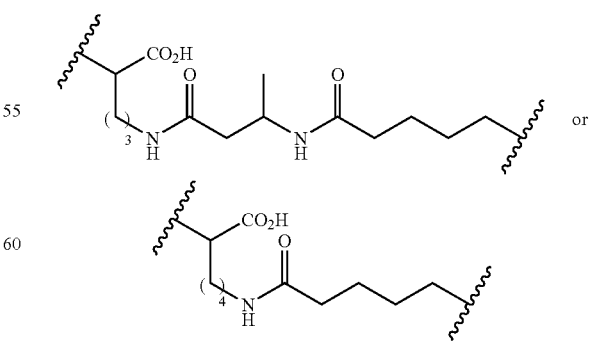

In certain embodiments, the present invention relates to compound IV, wherein n represents independently for each occurrence 2, R represents independently for each occurrence hydrogen, Y is —C(O)—, A is a covalent bond, and X represents independently for each occurrence:

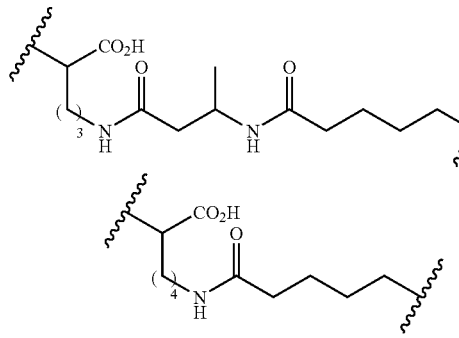

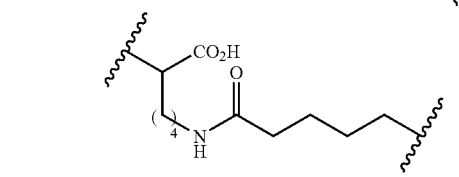

In certain embodiments, the present invention relates to compound IV, wherein n represents independently for each occurrence 2, R represents independently for each occurrence hydrogen, Y is —C(O)—, Z is an anti-infectived, and X represents independently for each occurrence:

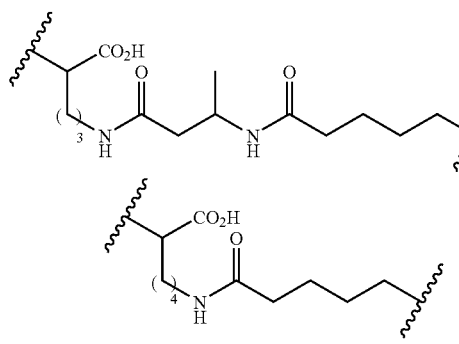

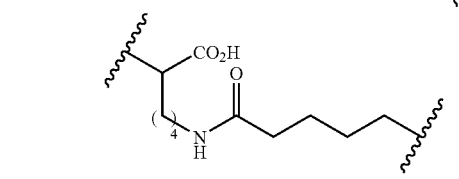

In certain embodiments, the present invention relates to compound IV, wherein n represents independently for each occurrence 2, R represents independently for each occurrence hydrogen, Y is —C(O)—, Z is an anti-tumor, and X represents independently for each occurrence:

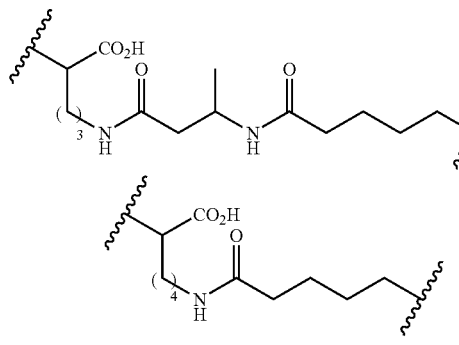

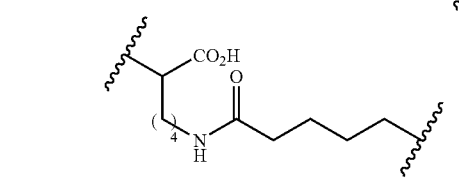

In certain embodiments, the present invention relates to compound IV, wherein n represents independently for each occurrence 2, R represents independently for each occurrence hydrogen, Y is —C(O)—, Z is an anti-inflammatory, and X represents independently for each occurrence:

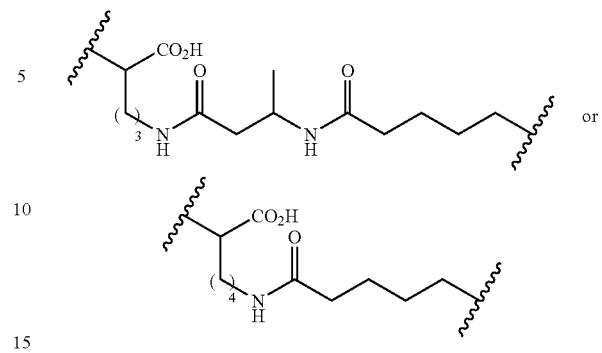

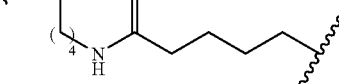

In certain embodiments, the present invention relates to compound IV, wherein Z is an anti-infective, anti-inflammatory, or anti-tumor agent.

In certain embodiments, the present invention relates to compound IV, wherein Z is selected from the group consisting of abacavir sulfate, abarelix, acarbose, acetaminophen, acetylsalicylic acid, acitretin, activated protein C, acyclovir, adefovir dipivoxil, adenosine, adrenocorticotrophic hormone, albuterol, alendronate sodium, allopurinal, alpha 1 proteinase inhibitor, alprazalom, alprostadil, altinicline, amifostine, amiodarone, amitriptyline HCL, amlodipine besylate, amoxicillin, amprenavir, anagrelide hydrochloride, anaritide, anastrozole, antisense oligonucleotide, aripiprazole, astemizole, atenolol, bupropion hydrochloride, buspirone, butorphanol tartrate, cabergoline, caffiene, calcitriol, candesartan, cilexetil, candoxatril, capecitabine, captopril, carbamazepine, carbidopa/Levodopa, carboplatin, carisoprodol, carvedilol, caspofungin, cefaclor, cefadroxil, cyclosporine, dalteparin sodium, dapitant, desmopressin acetate, diazepam, ABT 594, diclofenac sodium, dicyclomine HCL, didanosine, digoxin, diltiazem hydrochloride, fentanyl, fexofenadine hydrochloride, filgrastim SD01, finasteride, flecainide acetate, fluconazole, fludrocortisone acetate, flumazenil, fluoxetine, flutamide, fluvastatin, fluvoxamine maleate, follitropin alfa/beta, formoterol, fosinopril, fosphenytoin sodium, furosemide, gabapentin, gadodiamide, gadopentetate dimeglumine, gadoteridol, ganaxolone, ganciclovir, gantofiban, gastrin CW17 immunogen, gemcitabine hydrochloride, gemfibrozil, gentamicin isoton, gepirone hydrochloride, pioglitazone hydrochloride, piperacillin sodium, pleconaril, poloxamer CW188, posaconazole, NN 304, pramipexole dihydrochloride, pravastatin sodium, prednisone, pregabalin, primidone, prinomastat, prochlorperazine maleate, valdecoxib, valproic acid, valsartan hydrochlorothiazide, valspodar, Vancomycin HCL, Vecuronium bromide, venlafaxine hydrochloride, verapamil HCL, vinorelbine tartrate, vitamin B12, vitamin C, voriconazole, warfarin sodium, xaliproden, and zafirlukast.

In certain embodiments, the present invention relates to compound IV, wherein A is:

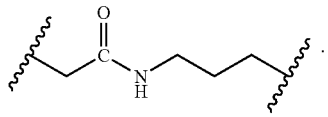

In certain embodiments, the present invention relates to compound IV, wherein Z is selected from the group consisitng of an anti-infective, anti-inflammatory, and anti-tumor agent; and A is:

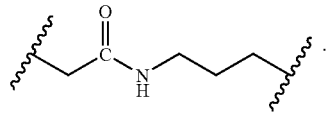

Methods of the Invention

One aspect of the present invention relates to a method of treating disease in a mammal, comprising the step of:
administering to said mammal a therapeutically effective amount of a compound of formula I, II, III, or IV.

In certain embodiments, the present invention relates to the aforementioned methods, wherein said disease is a bacterial infection, viral infection, cancer or characterized by inflamation.

In certain embodiments, the present invention relates to the aforementioned methods, wherein said disease is cancer.

In certain embodiments, the present invention relates to the aforementioned methods, wherein said mammal is a human.

In certain embodiments, the present invention relates to the a formulation, comprising a compound of formula I, II, III, or IV and a pharmaceutically acceptable excipient.

A method of generating a magnetic resonance image of a human or non-human animal body, comprising the steps of
administering into the body of a subject in need of magnetic resonance imaging a compound of formula II or IV, and generating a magnetic resonance image.

In certain embodiments, the present invention relates to the aforementioned methods, wherein said subject is a human.

In certain embodiments, the present invention relates to the aforementioned methods, wherein said compound of formula II wherein M is selected from the group consisting of $Gd^{3+}$, $Mn^{2+}$, $Fe^{2+}$, or $Cr^{3+}$.

In certain embodiments, the present invention relates to the aforementioned methods, wherein said compound of formula II wherein M is $Gd^{3+}$.

In certain embodiments, the present invention relates to the aforementioned methods, wherein said compound of formula II wherein M is selected from the group consisting of In-111, Tc-99m, I-123, I-125 F-18, Ga-67, Ga-68, I-131, Re-186, Re-188, Y-90, Bi-212, At-211, Sr-89, Ho-166, Sm-153, Cu-67, and Cu-64.

In certain embodiments, the present invention relates to the aforementioned methods, wherein said compound of formula II wherein M is Tc-99m.

Treatment of Bacterial Infection

The antibacterial properties of the compounds of formula I, II, III and IV may be determined from a bacterial lysis assay, as well as by other methods, including, inter alia, growth inhibition assays (e.g., such as described by Blondelie et al. (1992) *Biochemistry* 31:12688), fluorescence-based bacterial viability assays (e.g., Molecular Probes BacLight), flow cytometry analyses (Arroyo et al. (1995) *J. Virol.* 69: 4095-4102), and other standard assays known to those skilled in the art.

The assays for growth inhibition of a microbial target can be used to derive an $ED_{50}$ value for the compound, that is, the concentration of compound required to kill 50% of the microbial sample being tested.

Alternatively, growth inhibition by an antimicrobial compound of the invention may also be characterized in terms of the minimum inhibitory concentration (MIC), which is the concentration of compound required to achieve inhibition of microbial cell growth. Such values are well known to those in the art as representative of the effectiveness of a particular antimicrobial agent (e.g., an antibiotic) against a particular organism or group of organisms. For instance, cytolysis of a bacterial population by an antimicrobial compound can also be characterized, as described above by the minimum inhibitory concentration, which is the concentration required to reduce the viable bacterial population by 99.9%. The value of $MIC_{50}$ can also be used, defined as the concentration of a compound required to reduce the viable bacterial population by 50%. In preferred embodiments, the compounds of the present invention are selected for use based, inter alia, on having MIC values of less than 25 μg/mL, more preferably less than 7 μg/mL, and even more preferably less than 1 μg/mL against a desired bacterial target, e.g., a Gram positive bacteria such as methicillin-resistant *Staphylococcus aureus* or *Streptococcus pneumoniae*.

Another parameter useful in identifying and measuring the effectiveness of the antimicrobial compounds of the invention is the determination of the kinetics of the antimicrobial activity of a compound. Such a determination can be made by determining antimicrobial activity as a function of time. In a preferred embodiment, the compounds display kinetics which result in efficient lysis of a microorganism. In a preferred embodiment, the compounds are bacteriocidal.

Furthermore, the preferred antimicrobial compounds of the invention display selective toxicity to target microorganisms and minimal toxicity to mammalian cells. Determination of the toxic dose (or "$LD_{50}$") can be carried using protocols well known in the field of pharmacology. Ascertaining the effect of a compound of the invention on mammalian cells is preferably performed using tissue culture assays, e.g., the present compounds can be evaluated according to standard methods known to those skilled in that art (see for example Gootz, T. D. (1990) *Clin. Microbiol. Rev.* 3:13-31). For mammalian cells, such assay methods include, inter alia, trypan blue exclusion and MTT assays (Moore et al. (1994) *Compound Research* 7:265-269). Where a specific cell type may release a specific metabolite upon changes in membrane permeability, that specific metabolite may be assayed, e.g., the release of hemoglobin upon the lysis of red blood cells (Srinivas et al. (1992) *J. Biol. Chem.* 267:7121-7127). The compounds of the invention are preferably tested against primary cells, e.g., using human skin fibroblasts (HSF) or fetal equine kidney (FEK) cell cultures, or other primary cell cultures routinely used by those skilled in the art. Permanent cell lines may also be used, e.g., Jurkat cells. In preferred embodiments, the subject compounds are selected for use in animals, or animal cell/tissue culture based at least in part on having $LD_{50}$'s at least one order of magnitude greater than the MIC or $ED_{50}$ as the case may be, and even more preferably at least two, three and even four orders of magnitude greater. That is, in preferred embodiments where the subject compounds are to be administered to an animal, a suitable therapeutic index is preferably greater than 10, and more preferably greater than 10, 1000 or even 10,000.

Antibacterial assays for the compounds of the invention can be performed to determine the bacterial activity toward both Gram-positive and Gram-negative microorganisms. Typical Gram-negative pathogens which may be sensitive to the antibacterial agents of the present invention can include, for example, species of genus *Escherichia*, genus *Enterobacter*, genus *Klebsiella*, genus *Serratia*, genus *Proteus* and genus *Pseudomonas*. For example, the subject compositions and methods can be used as part of treatment and prevention regimens for infections by some of the most frequently encountered Gram-negative and Gram-positive organisms, including those involving *Escherichia coli* (*E. Coli*), *Klebsiella peumoniae* (*K. peumoniae*), *Serratia marcescens*, *Enterobacter aerogenes* and *Enterobacter cloacae* (*E. aerogenes* and *E. cloacae*), *Pseudomonas aeruginosa* (*P. aeruginosa*), *Neisseria meningitidis* (*N. meningitidis*), Group B *Streptococcus aureus* and *Staphylococcus aureus*, *Streptococcus pneumonia*, *Streptococcus pyogenes*, *Corynebacter diphtheriae*, *Gardnierella vaginalis*, *Actinetobacter* spp., *Bordella pertussis*, *Haemophilus aegyptius*, *Haemophilus influenza*, *Haemophilus ducreyi*, *Shigella* spp, *Serratia* spp., and *Propionibacterium acnes*.

The above list of pathogens is purely illustrative and is in no way to be interpreted as restrictive.

Examples of conditions which can be treated include illnesses of the respiratory passages and of the pharyngeal cavity; otitis, pharyngitis, pneumonia, peritonitis, pyelonephritis, cystitis, endocarditis, systemic infections, bronchitis, arthritis, local inflammations, skin infections, conjuntivitis, and infections of any surgically created vascular access for the purpose of hemodialysis.

In preferred embodiments, the antibacterial agents of the present invention are selected based on their ability to inhibit growth of Gram-positive bacteria. Such Gram-positive bacteria include bacteria from the following species: *Staphylococcus, Streptococcus, Micrococcus, Peptococcus, Peptostreptococcus, Enterococcus, Bacillus, Clostridium, LactobacilIus, Listeria, Erysipelothrix, Propionibacterium, Eubacterium*, and *Corynebacterium*.

A variety of Gram-positive organisms are capable of causing sepsis. The most common organisms involved in sepsis are *Staphylococcus aureus, Streptococcus pneumoniae*, coagulase-negative staphylococci, beta-hemolytic streptococci, and enterococci, but any Gram-positive organism may be involved. (see, e.g., Bone, (1993) *J. Critical Care* 8:51-59). Thus, it is specifically contemplated that the subject compositions and methods can be used as part of a therapeutic treatment or prevention program for sepsis involving Gram-positive bacteria.

Accordingly, in one embodiment, *S. aureus* is used as a model of a Gram-positive microorganism in testing/selecting the compounds of the present invention. This bacteria is also a significant clinical target as well because it is refractive to most systemic antibiotic treatments. *Staphylococcus aureus* is the most frequent cause of skin, wound, and blood infections and the second most frequent cause of lower respiratory tract infections, and the microorganism tends to prey on immunocompromised and institutionalized patients. Thus, the subject compounds can be used to treat such infections caused by *Staphylococcus*, as well as in the treatment of conjunctivitis, outer ear infections and the like.

One of the key contributors to the increase in mortality and morbidity due to bacterial infections is the increasing prevalence of drug-resistant bacteria. Examples of the seriousness of antibiotic resistance are methicillin-resistant *staphylococci* (MRSA), and the emergence of vancomycin-resistant *S. aureus* which have become resistant to virtually all currently used antibiotics. Thus, methicillin-resistant *S. aureus* may also be used as an antibiotic-resistant model organism for selecting the subject compounds. In a preferred embodiment, the antibacterial agents of the present invention can be used in the treatment and/or prevention of endocarditis, e.g., which may be caused by MRSA.

The heavy use of vancomycin to treat MRSA infections has in turn contributed to the emergence of new strains of enterococci, the third most prevalent cause of bacterial infection in the U.S., which are resistant to vancomycin. *Enterococcus* causes as many as 15 percent of bacterial endocarditis cases; it is also the cause of meningitis, and infections in the urinary tract, stomach and intestines. Infections caused by these vancomycin-resistant enterococci (VRE) frequently do not respond to any current therapies, and in many cases prove fatal. Accordingly, the subject compounds can be selected using an assay based on *E. faecalis* sensitivity, and in particular, the vancomycin-resistant isolates found in clinical settings such as a hospital.

The subject compositions may also be selected for treatment of infection by *Streptococcus*. *Streptococcus* species are found associated in a great variety of pathologic conditions among which are gangrene, puerperal infections, subacute bacterial endocarditis, septic sore throat, rheumatic fever, and pneumonia. Agents which are active against *Streptococcus* species are, therefore, greatly needed.

To further illustrate, *E. coli* and *P. aeruginosa* are examples of Gram-negative organisms which may be sensitive to the subject antibacterial agents. *P. aeruginosa* is a particularly problematic source of disease in such conditions as lung infections in patients with cystic fibrosis, burn infections, eye and urinary tract infections, and infection with *P. aeruginosa* may result in serious septicemia. Moreover, imipenem-resistant *P. aeruginosa* are increasing in the clinical field. Enteropathogenic *E. coli* are responsible for outbreaks of diarrhea in infants and newborns, and diarrhea, including "traveler's diarrhea", in adults. *E. coli* may be invasive and toxin-producing, causing sometimes fatal infections, such as cystitis, pyelitis, pyelonephritis, appendicitis, peritonitis, gallbladder infection, septicemia, meningitis and endocarditis.

In still other embodiments, the subject compounds can be used in the treatment of infections caused by *Serratia* spp. For instance, *S. marcescens* is a source of ophthalmic and other topical infections, and can be readily provided in assays intended to identify those compounds of the present invention which are bactercidal at suitable concentrations agains that bacteria.

The subject compounds may also be used in the treatment of external ear infections (otitis externa), or in the treatment of sexually transmitted diseases such as *Niesseria gonorrhea* and trichomonas infections.

Certain compounds according to the invention may also be selected on the basis of their activity against typical and atypical *Mycobacteria* and *Helicobacter pylori*, and also against bacteria-like microorganisms, such as, for example, Mycoplasma and Rickettsia. They are therefore particularly suitable in human and veterinary medicine for the prophylaxis and chemotherapy of local and systemic infections caused by these pathogens. *Mycobacterium boris*, like *M. tuberculosis, M. africanum, M. ulcerans*, and *M. leprae*, is a strict pathogen. *M. bovis* is a significant pathogen throughout much of the world, causing tuberculosis, primarily in cattle.

In other embodiments, the subject compositions can be used in the treatment/prevention of infection by *Salmonella*. *Salmonella* spp. cause food poisoning, resulting in nausea, vomiting, diarrhea and sometimes-fatal septicemia. For instance, *S. typhi* is the etiological agent of typhoid fever.

The compositions and methods of the present invention may also be useful in the treatment of infection by *Shigella*. *Shigella* spp., including *S. dysenteriae*, are common waterborne pathogenic agents, causing bacillary dysentery as well as bacteremia and pneumonia. In the United States and Canada, *S. sonnei* and *S. flexneri* have become the most common etiological agents in bacillary dysentery.

Bacteria of the genus *Yersinia* are also pathogens which may be treated by the subject compositions. *Y. Enterocolitica*, for example, is an enteric pathogen. Infection with this microorganism causes severe diarrhea, gastroenteritis and other types of infections such as bacteremia, peritonitis, cholecystis, visceral abscesses, and mesenteric lymphadenitis. Septicemia with 50% mortality has been reported. *Y. pestis* is the etiologic agent of bubonic, pneumonic, and septicemic plague in humans.

Treatment of Cancer

The present invention further provides methods of modulating the survival and/or proliferation of a transformed tumor cells with compounds of formula I, II, III or IV. Such tumors include, but are not limited to, tumors of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostrate, lung, breast, central nervous system, or brain.

Treatment of Inflammatory Disorders

The compounds, compositions and methods of the invention are useful for treating inflammatory diseases or reactions, in particular those with overproduction of inflammatory mediators, including, but not limited to, IL-2, IL-5, IL-8, IFN-gamma, and TNF-alpha. Store-operated calcium influx activates a number signaling pathways in inflammatory cells, resulting in the production of proinflammatory cytokines and chemokines, release of other soluble inflammatory mediators such as autocoids, proteolytic enzymes, and toxic proteins, and upregulation of cell surface molecules, including adhesion molecules and receptors, that play key roles in inflammatory and autoimmune diseases. Important calcium-regulated signaling molecules include the transcription factors NFAT and NF-.kappa.B, and the stress kinases JNK and p38. JNK plays an important role in upregulation of the transcription factor activator protein-1 (AP-1), and is involved in TNF-.alpha. production (Minden A and Karin M, Biochim. Biophys. Acta 1333:F85-104, 1997; Lee J C and Young P R, J. Leukoc. Biol. 59:152-7, 1996). In activated T cells, NFAT is required for the transcriptional regulation of IL-2, IL-3, IL-4, IL-5, IL-8, IL-13, TNF alpha, and GM-CSF (Crabtree G R and Clipstone N A, Annu. Rev. Biochem. 63:1045-83, 1994). NF-kappa B is essential for the transcriptional regulation of the proinflammatory cytokines, including IL-1, IL-6, IL-8, IFN.gamma. and TNF-.alpha., as well as cell adhesion molecules VCAM-1 and ICAM-1, the IL-2 receptor alpha chain, and the cell growth regulator c-Myc (Baldwin A S, J. Clin. Invest. 107:3-6, 2001; Barnes P J and Karin M, N. Engl. J. Med. 336:1066-71, 1997). AP-1 transcriptionally regulates IL-2 and production of matrix metalloproteinases (Palanki M S, Curr. Med. Chem. 9:219-27, 2002). Mast cells and basophils express the high affinity IgE receptor (Fc.epsilon.RI) and synthesize histamine. Cross-linking Fc.epsilon.RI by antigen results in calcium influx, degranulation, and production of proinflammatory eicosanoids. In addition to histamine, human mast cell secretory granules also contain the neutral proteases tryptase, chymase and carboxypeptidase. Tryptase has been implicated as a fibrogenic factor. Mast cells and basophils thus participate not only in allergic disease, but also in chronic and fibrotic disorders affecting several organs, including the lungs (Marone G, Int. Arch. Allergy Immunol. 114:207-17, 1997). Compounds that can effectively block calcium-influx and activation of NFAT, NF-.kappa.B, AP-1, and mast cell/basophil degranulation thus provide potential medical treatments for various inflammatory and autoimmune disorders.

Transcription factors such as NF-.kappa.B are activated by extracellular signals or cell-to-cell interactions that are converted into intracellular activation signals through receptor molecules located in the cell membrane. It has been proposed that bacterial toxin such as endotoxin, induces calcium fluxes in monocytes and the nuclear translocation of NF-.kappa.B, a key step in the generation of the inflammatory response. Under acute condition, endotoxin-induced inflammatory process could lead to serious medical condition like sepsis. The number of known genes being transcribed after NF-.kappa.B activation is increasing steadily. These genes includes cytokines (such as IL-1, TNF-.alpha., etc.), chemokines (IL-8 for example), growth factors, cellular ligands, and adhesion molecules; many of these genes are involved in the pathogenesis of rheumatoid arthritis (RA). To date, many other inflammatory disorders are believed to relate to NF-.kappa.B action (for recent reviews, see Yamamoto Y and Gaynor R B, Curr. Mol. Med. 1(3):287-96, 2001; Baldwin A S, J. Clin. Invest. 107:3-6, 2001). For example, Pneumococci cause damage to the ear in otitis and in association with bacterial meningitis. The pathogenesis of injury involves host responses to the cell wall and pneumolysin. Release of cell wall components, particularly during antibiotic-induced bacterial lysis, leads to an influx of leukocytes and subsequent tissue injury. The signal transduction cascade for this response is becoming defined and includes CD14, Toll-like receptors, NF-.kappa.B, and cytokine production. Decreasing the sequelae of otitis can be achieved by an effective blockage of pneumococcal-induced inflammation. We have demonstrated that SOC inhibitors are effective in blocking NF-.kappa.B activation in Jurkat cells, and thus can be considered as potential medical treatments of inflammatory conditions, such as RA and Crohn's disease, where NF-.kappa.B activation plays a crucial role.

The nuclear factor of activated T cells (NFAT) proteins are a family of transcription factors whose activation is controlled by calcineurin, a calcium-dependent protein phosphatase (Rao A et al., Annu. Rev. Immunol. 15:707-47, 1997; Stankunas K et al., Cold Spring Harb. Symp. Quant. Biol. 64:505-16, 1999). Originally identified in T cells as inducers of cytokine gene expression, NFAT proteins play varied roles in cells outside of the immune system (Horsley V and Pavlath G K, J. Cell Biol. 156:771-4, 2002; Graef I A et al., Curr. Opin. Genet. Dev. 11:505-12, 2001). Recently, using immunofluorescence/confocal microscopy, cyclosporin A and tacrolimus were shown to block the nuclear translocation of calcineurin and NFAT in cultured keratinocytes (Al-Daraji W I et al., J. Invest. Dermatol. 118:779-88, 2002). The results showed that a variety of cell types in normal and psoriatic skin expressed calcineurin and NFAT1, but expression was particularly prominent in keratinocytes. The principal cyclosporin A and tacrolimus binding proteins cyclophilin A and FKBP12 were also expressed in keratinocytes and non-immune cells in skin. NFAT1 was predominantly nuclear in normal basal epidermal keratinocytes. Increased nuclear localization of NFAT1 was observed in suprabasal keratinocytes within lesional and to a lesser extent nonlesional psoriatic epidermis compared to normal skin, suggesting increased activation of calcineurin in psoriatic epidermal keratinocytes. Agonists that induce keratinocyte differentiation, specifically 12-O-tetradecanoyl-phorbol-13-acetate (TPA) plus ionomycin, raised intracellular calcium, induced nuclear translocation of NFAT1 and calcineurin in keratinocytes, and was inhibited by pretreatment with cyclosporin A or tacrolimus. In contrast, in human dermal fibroblasts, TPA plus ionomycin or TPA did not significantly alter the proportion of nuclear-associated NFAT1. These results indicate that calcineurin is functionally active in human keratinocytes by inducing nuclear translocation of NFAT1, and that regulation of NFAT1 nuclear translocation in skin is cell type specific. Inhibition of this pathway in epidermal keratinocytes may account, in part, for the therapeutic effect of cyclosporin A and tacrolimus in skin diseases such as psoriasis. SOC inhibitors which can effectively inhibit NFAT activation provide an alternative pharmacological treatment for inflammatory conditions such as psoriasis.

Mast cells and/or basophils have been implicated in the expression of a wide variety of biological responses, including immediate hypersensitivity reactions, host responses to parasites and neoplasms, angiogenesis, tissue remodeling, and immunologically non-specific inflammatory and fibrotic conditions. Recent findings suggest that an important mechanism by which mast cells influence such biological responses is through the production of a broad panel of multifunctional cytokines. In contrast, the extent to which basophils can produce cytokines is uncertain (Galli S J et al., Curr. Opin. Immunol. 3:865-72, 1991). Mast cell-associated mediators are generally classified into two groups: the preformed mediators, which are stored in the cells' cytoplasmic granules and are released upon exocytosis, and the newly synthesized mediators, which are not stored but are produced and secreted only after appropriate stimulation of the cell. We now report that tumor necrosis factor alpha (TNF-alpha)/cachectin represents a new type of mast cell-associated mediator, in that IgE-dependent mast cell activation results in the rapid release of preformed stores of the cytokine followed by the synthesis and sustained release of large quantities of newly formed TNF-alpha. We also demonstrate that challenge with specific antigen induces higher levels of TNF-alpha mRNA at skin sites sensitized with IgE in normal mice or mast cell-reconstituted genetically mast cell-deficient WBB6F1-W/W1' mice than at identically treated sites in WBB6F1-W/W1' mice that are devoid of mast cells. These findings identify mast cells as a biologically significant source of TNF-alpha/cachectin during IgE-dependent responses and define a mechanism whereby stimulation of mast cells via the FC epsilon R.sup.1 can account for both the rapid and sustained release of this cytokine (Gordon J R and Galli S J, J. Exp. Med. 174:103-7, 1991).

Mast cells are widely regarded as important effector cells in immune responses associated with Th2 cells and IgE. Recent work shows that they can also contribute significantly to the expression of innate immunity. Furthermore, survival in a model of acute bacterial infection that is dependent on complement and mast cells can be greatly enhanced by long-term treatment of mice with the kit ligand (stem cell factor) at least in part because of the effects of such treatment on mast cell numbers and/or function. These findings not only indicate that mast cells can represent a critical component of host defense in natural immunity but also suggest that mast cell function in this setting can be manipulated for therapeutic ends (Galli S J et al., Curr. Opin. Immunol. 11:53-9, 1999). The release of pro-inflammatory mediators by mast cell degranulation is considered a calcium-dependent process. Compounds, such as SOC inhibitors that prevent mast cell degranulation, represent novel potential medical treatments for inflammatory, allergic and immune disorders where mast cells are implicated.

In certain embodiments, the compounds, compositions and methods are useful for treating any condition arising from increased activity of the lymphocyte activation pathway downstream of calcium entry such as NFAT (nuclear factor of activated T cells). In certain embodiments the compounds are also useful for treating inflammation arising from other calcium-dependent processes, including, but not limited to, mast cell degranulation and leukocyte secretion, as well as calcium-dependent elaboration of proinflammatory adhesion molecules, chemokines and cytokines by a variety of non-hemopoietic cells, including endothelial and epithelial cells.

Moreover, the compounds, compositions and methods of the present invention can also be used to prevent and/or treat inflammatory pulmonary disease or reactions (e.g., asthma, allergic rhinitis, chronic obstructive pulmonary disease, and adult respiratory distress syndrome), inflammatory musculoskeletal disease or reaction (e.g., exercise-induced injury, rheumatoid arthritis, psoriatic arthritis, osteoporosis and osteoarthritis), inflammatory gastrointestinal disease or urogenital reaction (e.g., enterocolitis, gastritis, Crohn's disease, interstitial cystitis, vaginitis, and ulcerative colitis), autoimmune disease or reactions (e.g., type II diabetes, inflammatory bowel disease, and psoriasis), irritable bowel syndrome, neurogenic inflammation and transplantation rejection reactions.

The compounds, compositions and methods of the present invention can also be used to prevent and/or treat inflammatory skin diseases (e.g., atopic dermatitis, eczema, contact dermatitis and allergic dermatitis), hyperproliferative skin diseases (e.g., psoriasis, basal cell carcinoma and squamous cell carcinoma), and skin irritation. Such conditions are well known to those of skill in the art and are described, e.g., in Champion et al., Eds. (1998) "Textbook of Dermatology", Blackwell Science, or in information provided by any of a number of organizations such as the American Academy of Dermatology (see, e.g., http://www.dermfnd.org/) and the American Cancer Society (see, e.g., http://www.cancer.org/). Further, the compounds and compositions of the present invention can be used to treat any symptom associated with any of these diseases or conditions, such as inflammation, redness, itching, pimples, crusts, scabs, dryness, burning, oozing, fluid, e.g., pus, discharge, pustules, blistering, rashes, disfiguration, scaling, dandruff, papules, plaques, lesions, thickenings, shedding, bumps, flaking, bleeding, tenderness, cuts, scratches, pain, cramps, irritation, swelling, blebs, vesicles, elevations, scarring, wrinkling, freckling, yellowing, blood vessel dilation, loss of normal function, and others.

The compounds, compositions and methods of the present invention are also useful for preventing and/or treating mucocutaneous inflammatory diseases such as asthma and allergic rhinitis as well as their associated symptoms. Descriptions of such conditions can be found in the Asthma and Allergy Foundation of America (see, e.g., http://www.aafa.org/) and are well known to those of skill in the art. Asthma is characterized by paradoxical narrowing of the bronchi that results in breathing difficulties. Typical symptoms associated with asthma include, e.g., wheezing, breathing difficulties, tightness of the chest, dry cough and shortness of breath after exercise. The compounds of the present invention can also be used to treat allergic rhinitis (hay fever). Allergic rhinitis results from an inflammatory reaction that occurs in the nasal passages in response to an allergic stimulus. Symptoms associated with allergic rhinitis include, e.g., sneezing, nasal congestion, nasal itching, nasal discharge and itching of the roof of the mouth and/or ears.

The compounds, compositions and methods of the present invention can also be used to prevent and/or treat skin aging, in particular extrinsic skin aging, as well as any symptoms associated with skin aging. Such symptoms include, for example, appearance of wrinkles and/or fine lines, slackening of cutaneous and subcutaneous tissue, sagging of the skin, atrophy of the epidermis, increased dryness of the skin, decrease in skin elasticity, increased fragility of capillaries, increased time of healing after injury, pigmentary alterations with areas of hyper- and hypopigmentation, appearance of a variety of benign, premalignant, and malignant neoplasms, and the like. Furthermore, at the histological level, aging results in thinning and deterioration of the skin, as well as in the reduction in cells and in blood supply, and a flattening in the junction between the dermis and epidermis.

In addition, compounds, compositions and methods of the present invention can be used to prevent and/or treat skin photodamage and any associated symptoms. Skin photodamage occurs with aging due to prolonged or repeated exposure to ultraviolet radiation. Signs of skin photodamage include, for example, wrinkling, yellowing, appearance of spots and mottling, elastosis, appearance of lines, leathery or dry appearance of the skin, and premature aging of the skin. At the histological level, skin photodamage may be reflected in tangled, thickened, abnormal elastic fibers, decreased collagen and increased glycosaminoglycan content (see, Tanaka et al. Arch. Dermatol. Res. 285:352-355, 2000).

The compounds, compositions and methods of the present invention are efficient for preventing and/or treating mucocutaneous inflammation and irritation caused by, for example, transdermal or transmucosal drug delivery, irritating drug delivery enhancers or irritating drug substances. The compounds and compositions of the present invention can also be used as excipients to enhance the potency of antiinflammatory drugs, such as corticosteroids, salicylates, colchicine, para-aminophenol, propionic acid, piroxicam, ketorolac, ketoprofen, cyclooxygenase inhibitors, indomethacin, and the like.

In yet another aspect, the present invention provides methods of treating an atopic disease, such as atopic dermatitis, allergic rhinitis or asthma, comprising: administering to a patient an HMG CoA reductase inhibitor (open-chain, lactone or combinations thereof) thereby treating the atopic disease. The HMG-CoA reductase inhibitors include, but are not limited to, mevastatin, lovastatin, fluvastatin, pravastatin, simvastatin, dalvastatin, cerivastatin and atorvastatin. The HMG CoA reductase inhibitor (open-chain, lactone or combinations thereof) can also be used to prevent and/or treat inflammatory skin diseases (e.g., atopic dermatitis, eczema, contact dermatitis and allergic dermatitis, a chronic obstructive pulmonary disease and adult respiratory distress syndrome), hyperproliferative skin diseases (e.g., psoriasis, basal cell carcinoma and squamous cell carcinoma), and skin irritation. Further, the HMG CoA reductase inhibitor (open-chain, lactone or combinations thereof) can be used to treat inflammatory gastrointestinal or urogenital disease or reaction such as inflammatory bowel disease, enterocolitis, gastritis, vaginitis, and interstitial cystitis.

Treatment of Viral Infections

The anti-viral agents of the present invention (the compounds of formulas I, II, III, and IV, and the pharmaceutically acceptable salts thereof) may be used to treat an infection by Herpes viruses (particularly both immunologically defined types of Herpes simplex, HSV-1 and HSV-2), and Poliomyelitis virus (including all three immunologically distinguishable types thereof), in addition to Varicella-zoster virus, Togaviruses, Cytomegalovirus (CMV), Epstein-Barr virus (EBV), Picornaviruses, Rhinovirus, Human papillona viruses and Hepatitis viruses, among others.

The anti-viral agents of the present invention are suitable for application to mammals (such as human beings, horses, cattle, dogs and rodents). The route of administration is usually oral or parenteral, although it is possible to administer the anti-viral agents by other administration routes, e.g., by topical application, depending on whether the preparation is used to treat internal or external viral infections, or nasal application. Topical application can be used for systemic treatment.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of

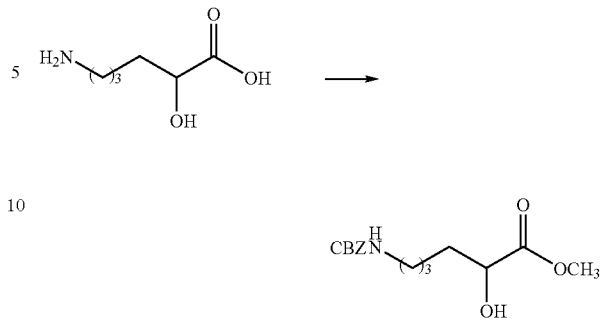

B. (S)-6-[[(Phenylmethoxy)carbonyl]amino]-2-hydroxyhexanoic acid

The aminohydroxy acid (7.5 g, 51.0 mmole) from Part A in a 1 N NaOH solution (50 ml) at 0° C. (ice bath) was adjusted to pH 10 with concentrated HCl and treated with benzyl chloroformate (8.40 ml, 95%, 55.9 mmole) in 1 ml portions at 15 minute intervals. Throughout the reaction, the pH was maintained at pH 9.8-10.2 by the addition of a 1N NaOH solution. When the addition was complete and pH had stabilized, the mixture was stirred at pH 10 at 0° C. for an additional 45 minutes, then washed with one portion of ether. The aqueous solution was acidified to pH 1 with concentrated HCl and extracted with EtOAc (2×). The EtOAc extract was washed with brine, dried and evaporated to give 4 g of the product.

C. (S)-6-[[(Phenylmethoxy)carbonyl]amino]-2-hydroxyhexanoic acid, methyl ester The crude hydroxy acid (4.0 g, 14.2 mm) from Part B and iodomethane (0.97 ml, 15.6 mmole, 1.1 eq) in dry DMF (15 ml) was treated with $K_2CO_3$ (2.55 g, 18.5 mmole, 1.3 eq) and the light yellow suspension was stirred for 4 hours at room temperature. The mixture was diluted with water and extracted with EtOAc (2×), the combined organic extracts were washed with water (2×), saturated $NaHCO_3$ and brine, then dried over anhydrous $Na_2SO_4$ and evaporated to give 3 g (80%) of the methyl ester as a viscous, pale yellow oil. TLC (1:1) EtOAc/hexane, Rf=0.5.

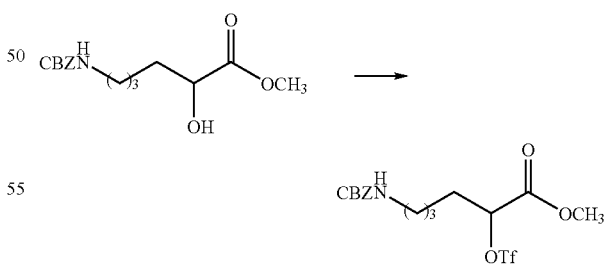

D. (S)-methyl-6-[(phenylmethoxy)carbonyl]amino]-2-triflyloxyhexanoate

A solution of the CBZ hydroxy ester from Part C (3.0 g, 10 mmol) and pyridine (0.71 g, 11 mmol) in methylene chloride (300 mL) at 0° C. was treated with triflic anhydride (3.1 g, 11 mmol) in methylene chloride (30 mL) for 1 h. After removal the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween.R™. and Pluronic.R™. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Exemplification

The invention now being generally described, it will be more readily understood by reference to the following examples, which are included merely for purposes of illustration of certain aspects and embodiments of the present invention, and are not intended to limit the invention.

EXAMPLE 1

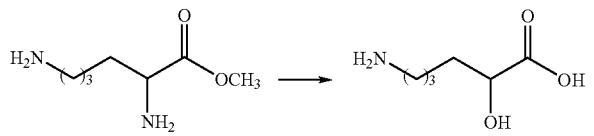

A. (−)-6-Amino-2-hydroxyhexanoic acid [*Chem. Pharm. Bull.* 1976, 24, 621]

An aqueous solution (100 ml) of sodium nitrite (25.9 g, 0.36 mole) was gradually added to a stirred solution of L-lysine hydrate (19.0 g, 0.097 mole) in 10% sulfuric acid (250 mL) at 45-50° C. over a 2 hr period. After addition was complete, the solution was stirred at 25° C. for 3 hr. Urea was added to the solution in order to decompose nitric acid formed in the reaction process and the aqueous solution was poured on to an ion exchange column (Amberlite IR-120, $H^+$ form, 200 ml). After the column was thoroughly washed with water, it was eluted with aqueous ammonium hydroxide until the eluant became negative to ninhydrin test. Combined fractions were evaporated in vacuo, which gave a yellow oil, 7.5 grams.

of the pyridinium triflate salt by filtration, the crude product was purified by silica gel chromatography to obtain the triflate (1.2 g, 31%). TLC: Rf 0.65 in dichloromethane/methanol (97:3).

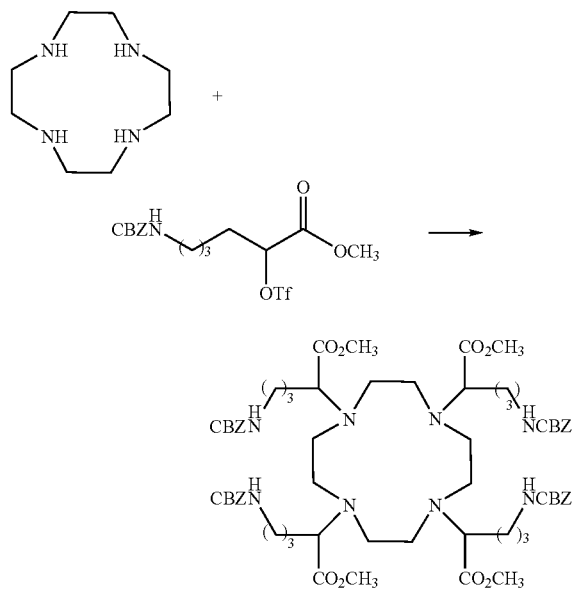

E. Protected DOTA Analog

Cyclen (50 mg, 0.29 mmol) in 10 mL of dry THF was treated with 1.6 M n-butyllithium (0.8 mL, 1.3 mmol) in hexane at 0° C. under nitrogen. The reaction mixture was then stirred at room temperature for 5 min. The flask was then immersed in a Dry-Ice/acetone bath and (S)-methyl-6-[(phenylmethoxy)carbonyl]amino]-2-triflyloxyhexanoate (0.68 g, 1.74 mmol) in THF (5 mL) and HMPA (1 mL) was added via syringe. The reaction mixture was allowed to reach room temperature where it was stirred for 1 hr. The reaction mixture was diluted with 50 mL of methylene chloride and washed with 10 mL of water and dried. Solvent was removed by vacuum and product was purified by chromatography (silica gel, methylene chloride/methanol, 90:10).

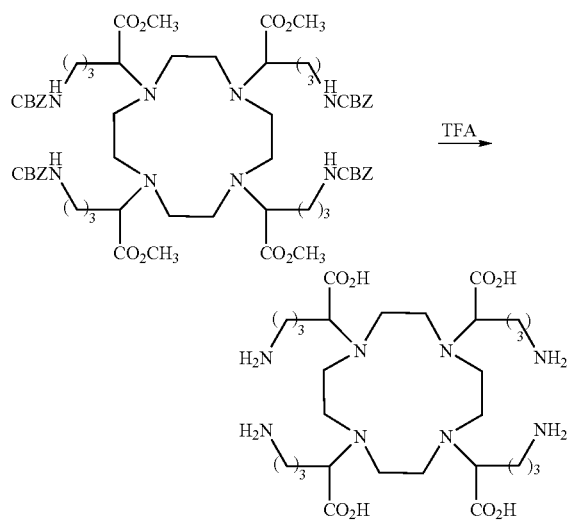

F. DOTA Analog

The protected DOTA analog was stirred in trifluoroacetic acid (10 mL) at 25° C. for two hours and excess trifluoroacetic acid blown off with a stream of nitrogen. The crude oil was washed with ether to give the DOTA analog.

EXAMPLE 2

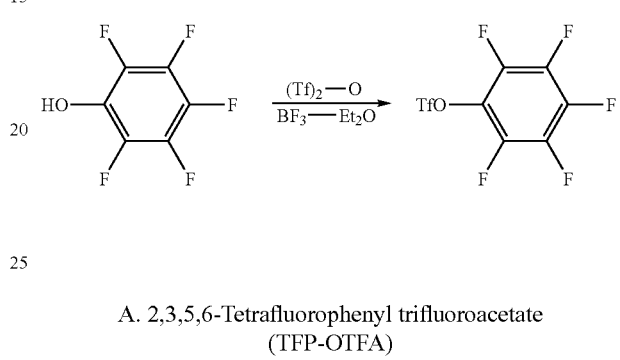

A. 2,3,5,6-Tetrafluorophenyl trifluoroacetate (TFP-OTFA)

Using a known procedure [*Nucleic Acids Res* 1993, 21, 145], a mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product was collected at 62° C./45 mm (45° C./18 mm) as a colorless liquid: yield: 81.3 (93%); d=1.52 g/mL; IR (CHCl$_3$) 3010, 1815, 1525, 1485, 1235, t180, and 955 cm$^{-1}$.

B. Synthesis of Biotin Tetrafluorophenyl Ester

Preparation of the TFP ester of biotin was accomplished as described by Wilbur [*Bioconj. Chem* 1997, 7, 692]. Biotin (1.0 g, 4.1 mmol) was dissolved in 20 mL of DMF (70° C.) under argon atmosphere. To the solution at 25° C., 1 mL (8 mmol) of triethylamine was added followed by the addition of 1.7 (6.1 mmol) of 2,3,5,6-tetrafluororophenyl trifluoroacetate. The reaction was stirred at room temperature for 30 min and solvent was removed under vacuum. The product was triturated in 10 mL of ether and filtered. The isolated product was dried under vacuum to yield 1.3 (80%) of biotin TFP ester as a colorless solid: mp: 185-187° C.; $^1$H NMR (DMSO-d$_6$, 0) 1.4-1.8 (m, 6H), 2.5 (m, 1H), 2.6-2.9 (m, 3H), 3.1 (m, 1H), 4.2 (m, 1H), 6.4 (d, 2H), 7.9 (m, 1 H); IR (KBr, cm-1) 3250, 2915, 1790, 1710, 1520, 1480, 1090.

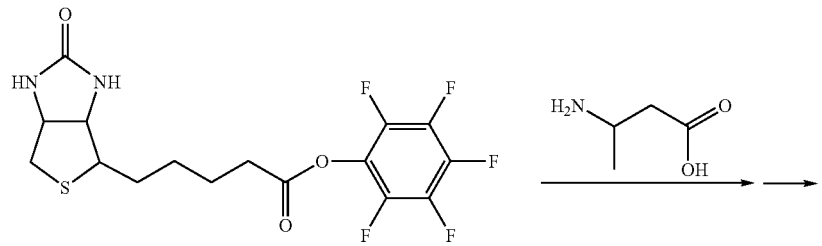

C. 3-(Biotinamido)butyric Acid

Preparation was accomplished as described by Wilbur [*Bioconj. Chem* 1997, 8, 572]. To a 0.13 g (1.3 mmol) quantity of 3-aminobutyric acid dissolved in 20 mL of DMF under argon atmosphere was added 0.4 mL (2.5 mmol) of triethylamine followed by 0.5 g (1.3 mmol) of biotin tetrafluorophenyl ester. The reaction was stirred at 25° C. for 24 h and the solvent was removed under vacuum. The residue was triturated with acetonitrile and filtered. The isolated solid was dried under vacuum to yield 0.5 g (98%) of product as a colorless solid, mp 161-163° C. $^1$H NMR (DMSO-d$_6$): O 7.6 (m, 1H), 6.2 (d, J=11.2 Hz, 2H), 3.9-4.2 (m, 3H), 2.6 (m, 2H), 2.35 (d, J=12.6 Hz, 1H), 1.7-2.1 (m, 4H), 0.7-1.5 (m, 10H).

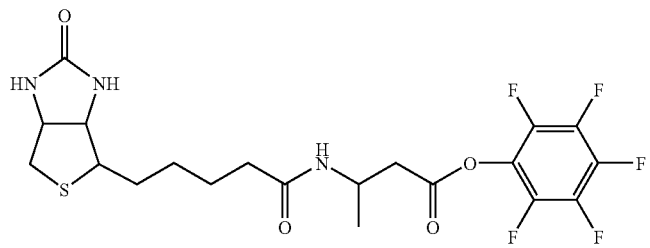

D. 3-(Biotinamido)butyrate Tetrafluorophenyl Ester 3-(Biotinamido)butyric acid (1.0 3.1 mmol) dissolved in 10 mL of DMF under argon atmosphere was added 1.0 (3.65 mmol) of TFP-OTFA, followed by 0.1 mL of triethylamine. The reaction mixture was stirred at 25° C. for 1 h and the solvent was removed under vacuum. The residue was extracted into CH$_3$Cl (4×20 mL). The combined CH$_3$Cl extracts were washed with saturated aqueous NaHCO$_3$ (2×10 mL) and water (2×10 mL). The CH$_3$Cl solution was dried over anhydrous Na$_2$SO$_4$, and the solvent was removed by vacuum. The product was dried to yield 1.1 g (80%) of as a colorless solid, mp 137-139° C. $^1$H NMR (DMSO-d$_6$): d 7.7 (m, 2H), 6.2 (d, J=13.2 Hz, 2H), 3.9-4.2 (m, 3H), 2.5-2.7 (m, 4H), 2.35 (d, J=12.6 Hz, 1H), 1.85 (t, J=7.0 Hz, 2H), 0.7-1.5 (m, 10H).

EXAMPLE 3

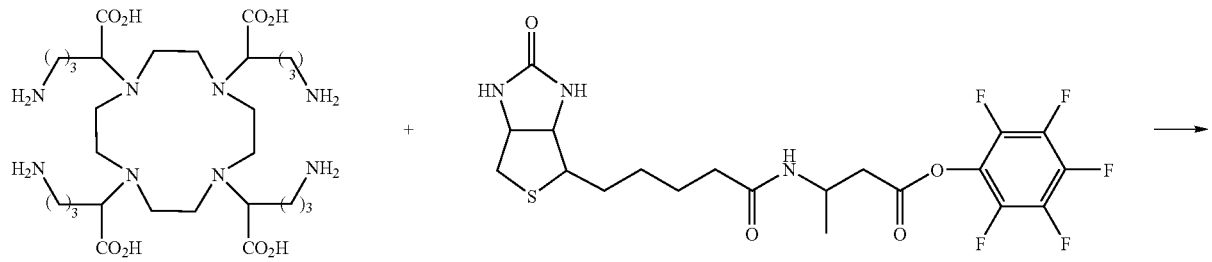

-continued

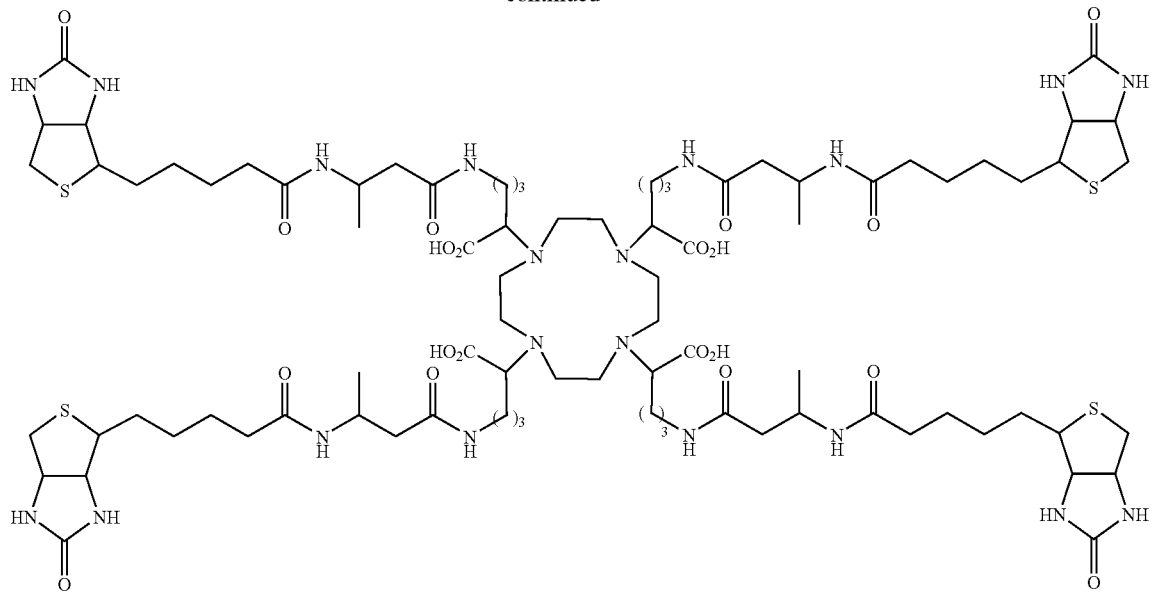

Biotin-DOTA

To a 0.5 g (0.65 mmol) quantity of the DOTA-amine analog acid dissolved in 20 mL of DMF under a nitrogen atmosphere was added 1 mL of triethylamine followed by 2.4 g (12.76 mmol) of 3-(biotinamido)butyrate tetrafluorophenyl Ester. The reaction was stirred at 25° C. for 24 h and solvent was removed under vacuum. The residue was triturated with acetonitrile and filtered. The isolated solid was dried under high vacuum. The product is purified by reverse phase HPLC.

EXAMPLE 4

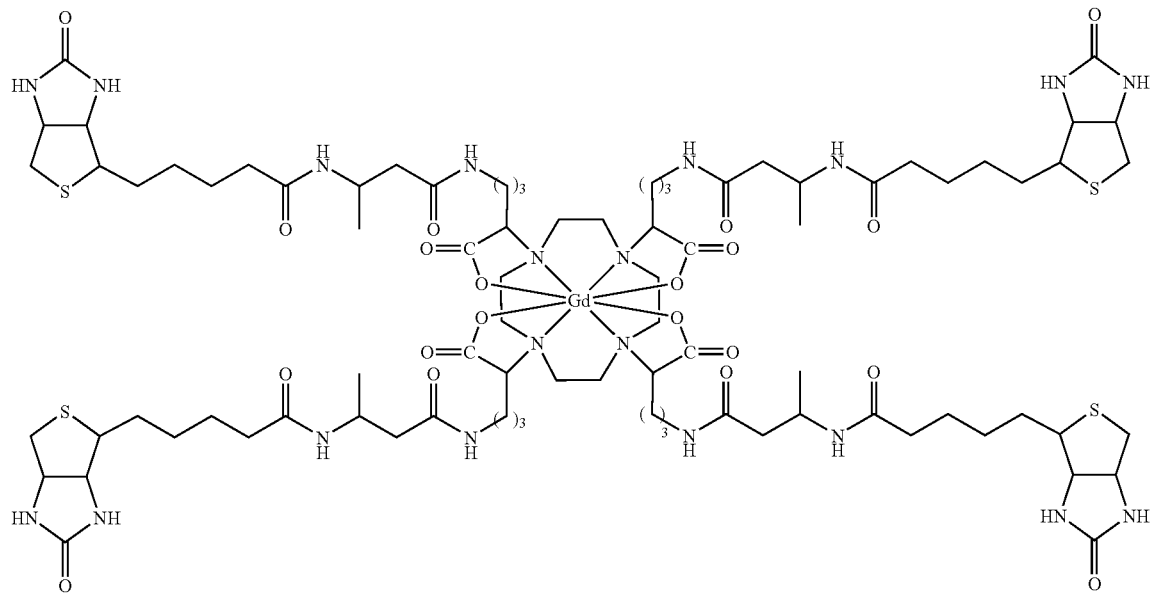

Gd-Biotin-DOTA

Chelation of gadolinium (Gd) is performed by incubating Biotin-DOTA with $GdCl_3$ in glycine/HCl buffer 50 mM, pH 3.5 at 80° C. for 3 hours. The conjugate is purified by reverse phase HPLC.

EXAMPLE 5

A. 6-(N-phtalimido)hexanoic Acid

A mixture of phthalic anhydride (56.4 g, 381 mmol), 6-aminocapric acid (50 g, 381 mmol), and triethylamine (54 ml) in toluene (200 mL) was refluxed for 1 hr in a 500-mL flask equipped with a Dean-Stark trap. The mixture was allowed to stand overnight at room temperature. The precipitate formed was filtered and washed with hexane followed by 1 N HCl, which gave 51 g (50%) of 6-(N-phtalimido)hexanoic acid; mp=110-112° C.

B. Isopropyl 2-bromo-6-(N-phtalimido)hexanoate

A mixture of 6-(N-phtalimido)hexanoic acid (10 g, 37.4 mmol), carbon tetrachloride (20 mL), and thionyl chloride (11.4 ml, 112.3 mmol) was refluxed for 1 hr. The mixture was cooled to room temperature and carbon tetrachloride (20 mL), NBS (8 g, 45 mmol), and 48% HBR (2 drops) was added. The mixture was refluxed for another two hrs. Once cooled to room temperature, isopropanol (60 ml) was added to the mixture and stirring continued at 25° C. for 30 min.

Volatiles were removed by roto-evaporation and the oil obtained was chromatographed on silica gel using ethyl acetate/hexane (10:90). Yield: 8.7 g (60%); $^1$H NMR ($CDCl_3$): δ(ppm) 1.19 (d, 3H), 1.35 (m, 2H), 1.68 (m, 4H), 2.25 (dd, 2H), 4.9 (m, 1H), 7.8 (m, 2H), 7.85 (m, 2H).

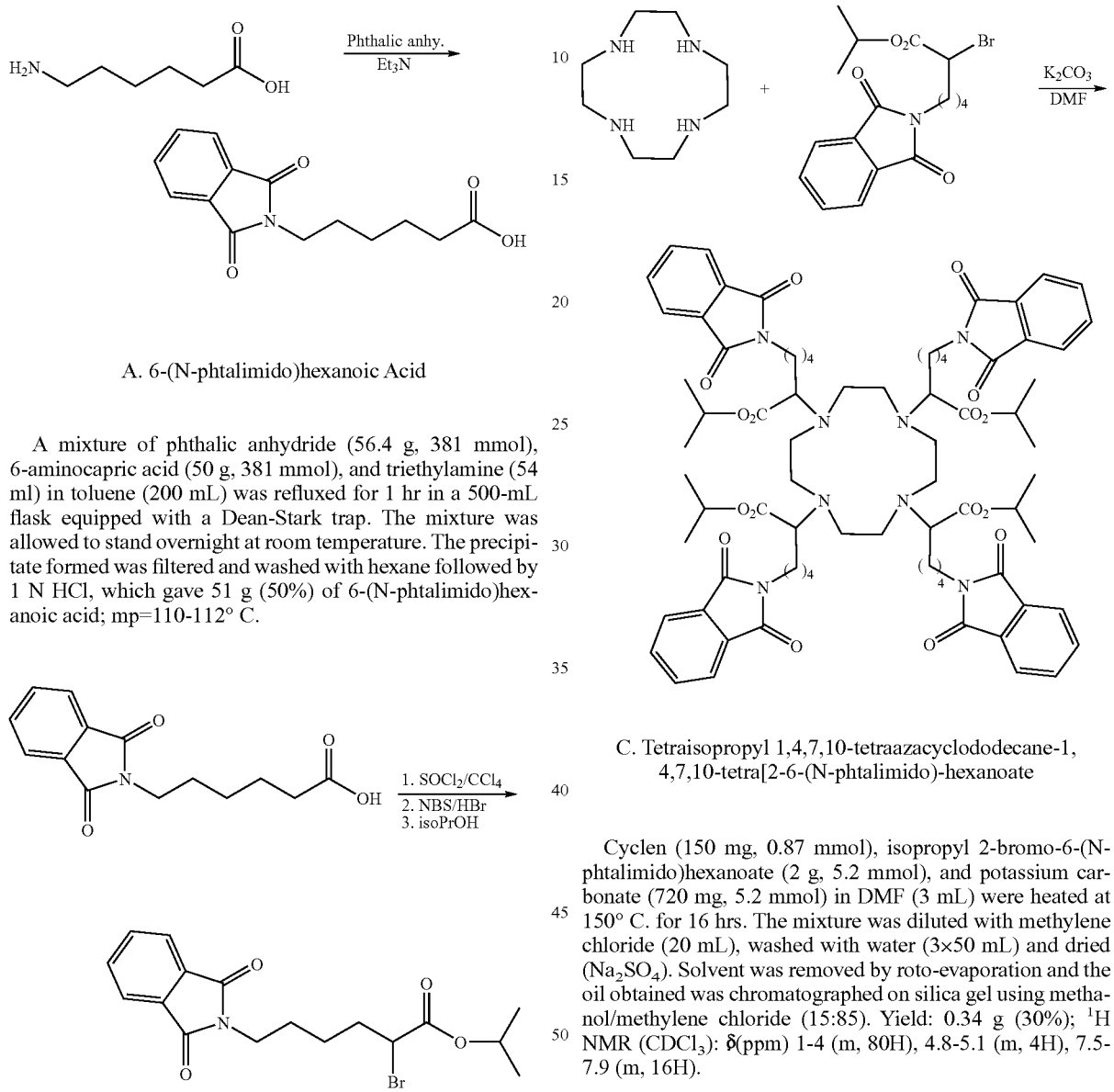

C. Tetraisopropyl 1,4,7,10-tetraazacyclododecane-1,4,7,10-tetra[2-6-(N-phtalimido)-hexanoate Cyclen (150 mg, 0.87 mmol), isopropyl 2-bromo-6-(N-phtalimido)hexanoate (2 g, 5.2 mmol), and potassium carbonate (720 mg, 5.2 mmol) in DMF (3 mL) were heated at 150° C. for 16 hrs. The mixture was diluted with methylene chloride (20 mL), washed with water (3×50 mL) and dried ($Na_2SO_4$). Solvent was removed by roto-evaporation and the oil obtained was chromatographed on silica gel using methanol/methylene chloride (15:85). Yield: 0.34 g (30%); $^1$H NMR ($CDCl_3$): δ(ppm) 1-4 (m, 80H), 4.8-5.1 (m, 4H), 7.5-7.9 (m, 16H).

EXAMPLE 6

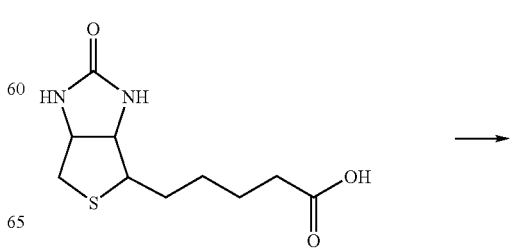

A. Biotin tetrafluorophenyl ester

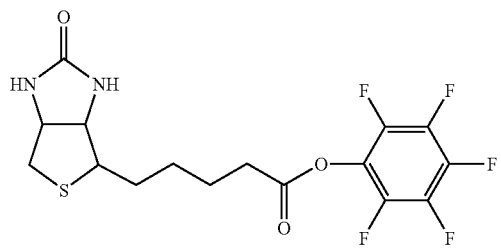

Biotin (1 g, 4 mmol) in 20 mL of DMF was heated at 70° C. until complete dissolution. The solution was cooled to room temperature and triethylamine (1 mL) was added followed by 2,3,5,6-tetrafluorophenyl trifluoroacetate (2 g, 8 mmol). The reaction was stirred for 30 min at 25° C. and solvents were removed under vacuum. The product was triturated in ether (20 mL) and was filtered and dried to yield 1.0 g (63%); mp 184-186° C.; $^1$H NMR (DMSO-$d_6$): δ(ppm) 1.4-1.8 (m, 6H), 2.5 (m, 1H), 2.6-2.9 (m, 34H), 3.1 (m, 1H), 4.2 (m, 6H), 6.4 (d, 2H), 7.9 (m, 1H).

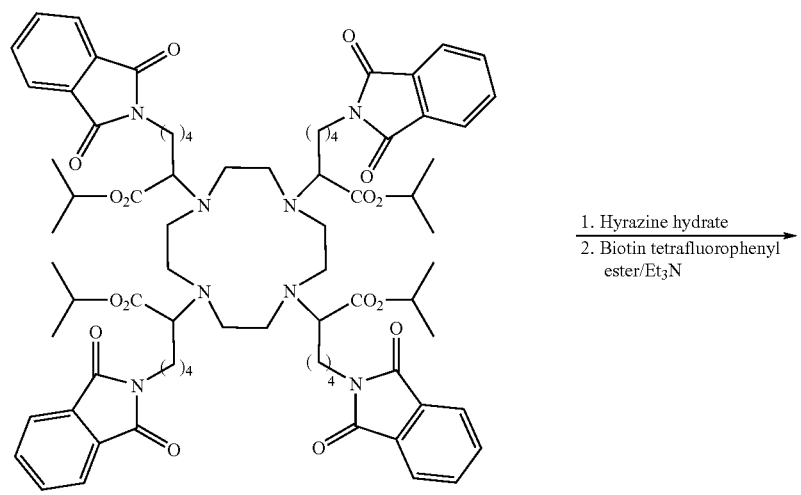

1. Hyrazine hydrate
2. Biotin tetrafluorophenyl ester/Et$_3$N

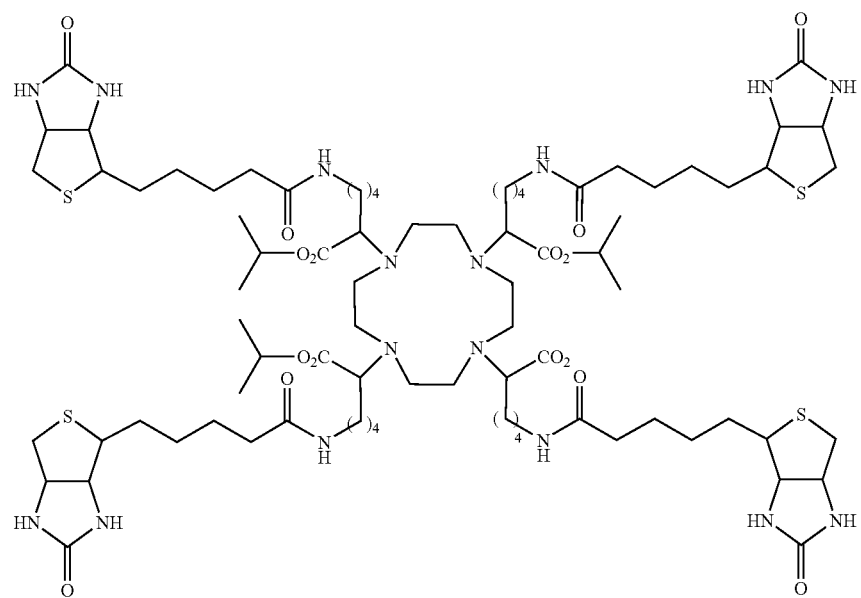

B. Tetraisopropyl 1,4,7,10-tetraazacyclododecane-1, 4,7,10-tetra[2-6-(biotinamido)-hexanoate A solution of tetraisopropyl 1,4,7,10-tetraazacyclododecane-1,4,7,10-tetra[2-6-(N-phtalimido)hexanoate (100 mg, 0.076 mmol) and hydrazine hydrate (20 µL, 0.38 mmol) in methanol (3 mL) was refluxed for 1 hr. Volatiles were removed by roto-evaporation and the resultant oil was dissolved in methylene chloride (20 mL) and solids were removed by filtration. After solvent evaporation, the oil, dissolved in DMF (10 mL), was treated with triethyl amine (1 mL) and biotin tetrafluorophenyl ester (0.26 g, 0.61 mmol) The mixture was stirred for 16 hrs. Solvent was removed under vacuum and the residue obtained was dissolved in methanol (5 mL) and was made basic (pH 9) by addition of a methanol/NaOH solution. The solvent was removed and the oil was chromatographed on silica gel (methanol/methylene chloride (10/90) to give 77.5 mg (60%) of product; mp=; $^1$H NMR (CDCl$_3$): δ(ppm) 1.4-1.8 (m, 32H), 2.3 (t, 16H), 2.7-3.2 (m, 12H), 4.3 (dd, 4H), 4.5 (dd, 4H), 5.2 (s,4H), 5.5 (s, 4H).

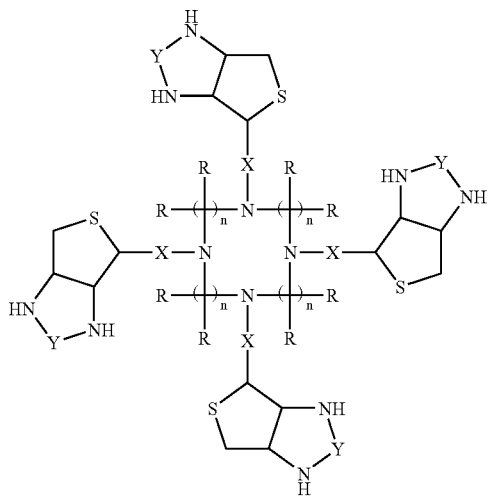

I wherein
R represents independently for each occurrence H or alkyl;
Y represents independently for each occurrence —C(O)— or —S(O)—;

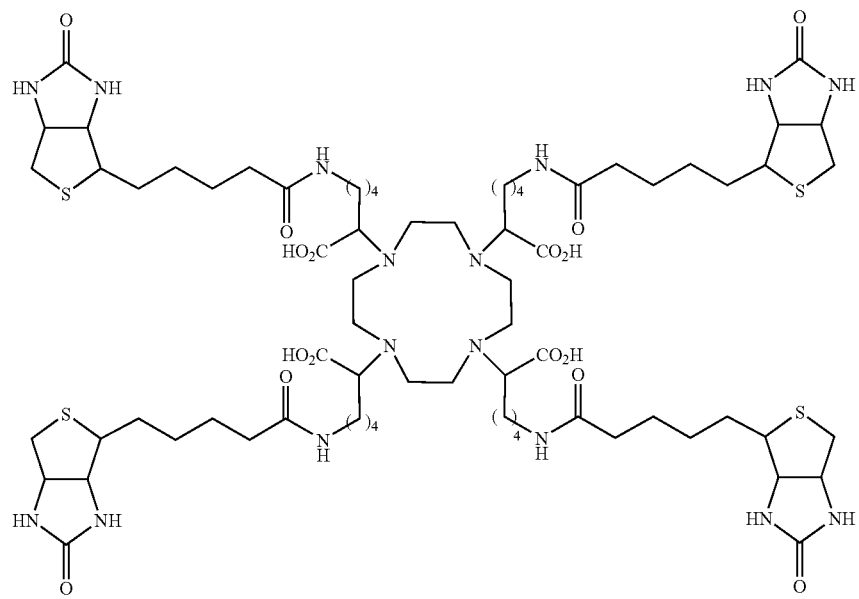

C. 1,4,7,10-tetraazacyclododecane-1,4,7,10-tetra[2-6-(biotinamido)]hexanoic acid tetra hydrochloric salt A solution of tetraisopropyl 1,4,7,10-tetraazacyclododecane-1,4,7,10-tetra[2-6-(biotinamido)hexanoate (50 mg) in 5 mL of 6 N HCl is refluxed for 4 hrs. Solvent is removed in vacuum to afford product.

n represents independently for each occurrence 1, 2, 3, or 4; and
X represents independently for each occurrence

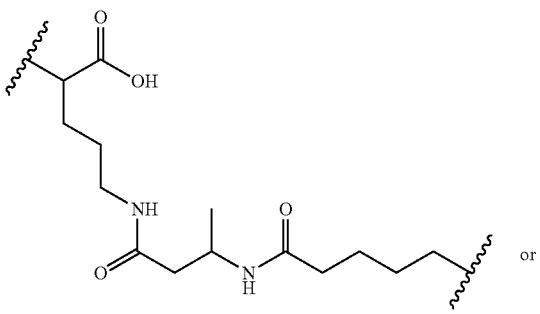

or

We claim:
1. A compound represented by formula I:

-continued

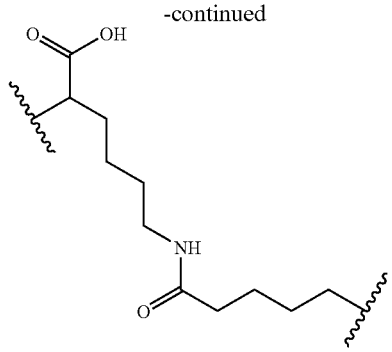

2. The compound of claim 1, wherein n is 2.

3. The compound of claim 1, wherein n is 2; and R is hydrogen.

4. The compound of claim 1, wherein n is 2; R is hydrogen; and Y is —C(O)—.

5. A formulation, comprising a compound of formula I and a pharmaceutically acceptable excipient; wherein a compound represented by formula I is:

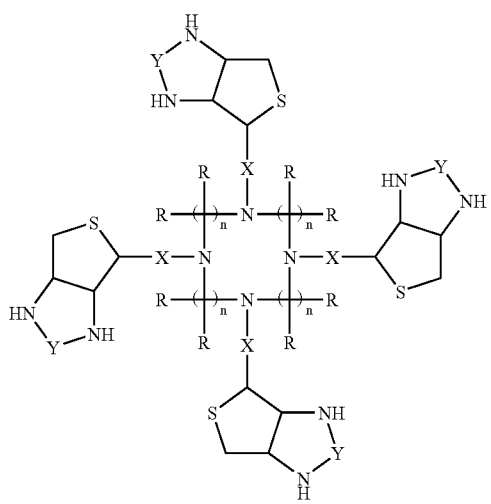

I wherein

R represents independently for each occurrence H or alkyl;

Y represents independently for each occurrence or —C(O)— or —S(O)—;

n represents independently for each occurrence 1, 2, 3, or 4; and represents independently for each occurrence

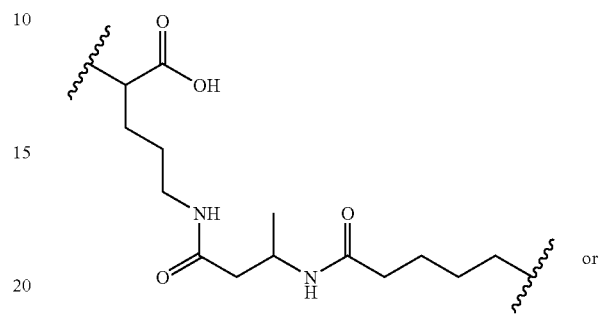

or

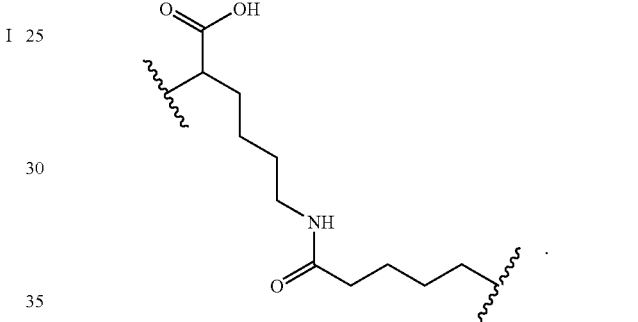

6. The formulation of claim 5, wherein n is 2.

7. The formulation of claim 5, wherein n is 2; and R is hydrogen.

8. The formulation of claim 5, wherein n is 2; R is hydrogen; and Y is —C(O)—.

* * * * *

UNITED STATES PATENT AND TRADEMARK OFFICE
CERTIFICATE OF CORRECTION

PATENT NO. : 7,438,893 B2
APPLICATION NO. : 10/956687
DATED : October 21, 2008
INVENTOR(S) : D. R. Elmaleh, T. M. Shoup and A. J. Fischman It is certified that error appears in the above-identified patent and that said Letters Patent is hereby corrected as shown below:

Title Page, Item 73, Assignee, should read:

The General Hospital Corporation, Charlestown, MA (US)

Signed and Sealed this
Twenty-ninth Day of May, 2012

David J. Kappos
*Director of the United States Patent and Trademark Office*